United States Patent [19]

Orwick et al.

[11] 4,404,012
[45] Sep. 13, 1983

[54] PROCESS FOR INCREASING SUGAR YIELD IN SUGARCANE

[75] Inventors: Philip L. Orwick, Morrisville, Pa.; Andrew R. Templeton, West Trenton, N.J.

[73] Assignee: American Cyanamid Company, Stamford, Conn.

[21] Appl. No.: 255,937

[22] Filed: Apr. 20, 1981

Related U.S. Application Data

[63] Continuation-in-part of Ser. No. 155,900, Jun. 2, 1980, abandoned.

[51] Int. Cl.³ .............................................. A01N 43/42
[52] U.S. Cl. .............................................. 71/92; 71/76; 546/278

[58] Field of Search ........................................ 71/76, 92

[56] References Cited

U.S. PATENT DOCUMENTS

| | | | |
|---|---|---|---|
| 3,495,969 | 2/1970 | Driscoll | 71/92 X |
| 4,029,492 | 6/1977 | Cross et al. | 71/92 |
| 4,188,487 | 2/1980 | Los | 71/92 X |
| 4,201,565 | 5/1980 | O'Neal | 71/76 |

*Primary Examiner*—Catherine L. Mills
*Attorney, Agent, or Firm*—H. G. Jackson

[57] ABSTRACT

There is provided a novel method for increasing sucrose yield in sugarcane by treating sugarcane a few weeks prior to harvest with a sucrose yield enhancing amount of a 2-(2-imidazolin-2-yl)pyridine compound.

7 Claims, No Drawings

PROCESS FOR INCREASING SUGAR YIELD IN SUGARCANE

This is a continuation-in-part of co-pending U.S. Ser. No. 155,900; filed June 2, 1980 now abandoned.

BACKGROUND OF THE INVENTION

Significant advances have been made over the past two decades in crop management techniques, improved farming practices, and chemical treatment, which provide increased sugar yields from sugarcane. In particular, soil enrichment programs, controlled irrigation and development of new varieties of sugarcane, have all aided in enhancing yields of sugar from cane. Additionally, it has been found that certain chemicals, when applied to growing cane several weeks prior to harvest, have improved sucrose levels in maturing sugarcane plants. Among the chemicals which have recently been found to be effective for this purpose are chlorocholine chloride, cetyltrimethylammonium bromide, trichlorobenzoic acid, $\beta,\beta,\beta$-trichloroethanephosphonic acid, N,N-bis(phosphoromethyl)glycine and tetradecyltrimethylammonium chloride. While these compounds have met with some success as ripening agents and sugar enhancing agents for sugarcane they are not, however, entirely satisfactory. It would therefore be advantageous if a novel class of chemicals could be found which would, when applied to sugarcane, enhance sugar yields therefrom.

Heretofore, chemicals selected for evaluation as sucrose yield enhancing agents for sugarcane have generally been those previously found to be plant growth regulating agents, herbicides, plant hormones or the like. However, among those compounds which have been found to be effective for the purposes mentioned above, only a very few have been found to be effective for enhancing sucrose yields from sugarcane.

To date, no correlation has been shown between a chemical structure and its phytotoxic, hormonal or growth regulating effects on plants and said compounds effectiveness as a sucrose enhancing agent for sugarcane. As such, there has been, heretofore, no effective method for predicting whether a chemical compound would be effective for enhancing sugar yield in sugarcane.

It is therefore an object of this invention to provide a new class of chemical agents effective for controlling the ripening of sugarcane and enhancing the sucrose yield therefrom.

SUMMARY OF THE INVENTION

This invention relates to a novel method for hastening the ripening of sugarcane in its latter stages of maturity and increasing the sucrose yield therefrom. In accordance with this invention the above-desirable effects can be obtained by applying to sugarcane, in the latter stages of its maturity, i.e. prior to harvest, an effective amount of a 2-(2-imidazolin-2-yl)pyridine compound represented by formula (I):

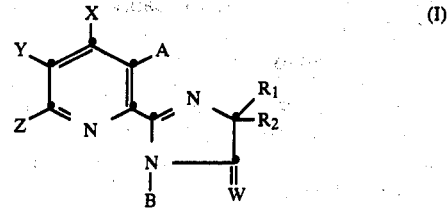

wherein
$R_1$ is $C_1-C_4$ alkyl;
$R_2$ is $C_1-C_4$ alkyl or $C_3-C_6$ cycloalkyl; and when $R_1$ and $R_2$ are taken together they may represent $C_3-C_6$ cycloalkyl optionally substituted with methyl;
A is $COOR_3$, $CONHR_6$, CHO, $CH_2OH$, $COCH_3$, $COC_6H_5$, CN, $CH_3$, $CH=NOH$, $CH_2COOH$, CONHOH, $CHR_8OH$, $CH_2CH_2COOH$,

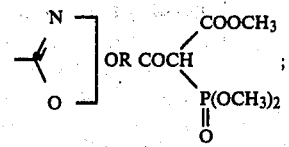

$R_3$ is hydrogen,
diloweralkylimino
$C_1-C_{12}$ alkyl optionally substituted with one of the following groups: $C_1-C_3$ alkoxy, halogen, hydroxy, $C_3-C_6$ cycloalkyl, benzyloxy, furyl, phenyl, halophenyl, loweralkylphenyl, loweralkoxyphenyl, nitrophenyl, carboxyl, loweralkoxycarbonyl, cyano or triloweralkylammonium;
$C_3-C_{12}$ alkenyl optionally substituted with one of the following groups: $C_1-C_3$ alkoxy, phenyl, halogen or loweralkoxycarbonyl or with two $C_1-C_3$ alkoxy groups or two halogen groups;
$C_3-C_6$ cycloalkyl optionally substituted with one or two $C_1-C_3$ alkyl groups;
$C_3-C_{10}$ alkynyl optionally substituted with one or two $C_1-C_3$ alkyl groups; or,
A cation selected from the group consisting of alkali metals, alkaline earth metals, manganese, copper, iron, zinc, cobalt, lead, silver, nickel, ammonium and organic ammonium;
$R_6$ is hydrogen, hydroxyl, $C_3$-alkenyl, $C_3$-alkynyl or $C_1-C_4$ alkyl optionally substituted with one hydroxyl or one chlorine group;
B is H, $COR_4$ or $SO_2R_5$; provided that when B is $COR_4$ or $SO_2-R_5$; A is $COOR_3$ in which $R_3$ is other than H, or a salt-forming cation, $CH_3$ or CN; W is O; and Y and Z are not alkylamino, hydroxyl; or hydroxyloweralkyl;
$R_4$ is $C_1-C_{11}$ alkyl, chloromethyl or phenyl optionally substituted with one chloro, one nitro or one methoxy group;
$R_5$ is $C_1-C_4$ alkyl or phenyl optionally substituted with one methyl group;
W is O or S;
$R_8$ is $C_1-C_4$-alkyl or phenyl;
X is hydrogen, halogen, hydroxyl or methyl, with the proviso that when Y and Z are taken together to form a ring and YZ is represented by the structure: $-(CH_2)_n-$, where n is 3 or 4, X is hydrogen;
Y and Z each represent members selected from the group consisting of hydrogen, halogen, $C_1-C_6$ alkyl, $C_1$–$C_4$ hydroxyloweralkyl, $C_1$–$C_6$ alkoxy, $C_1$–$C_4$ alkylthio, phenoxy, $C_1$–$C_4$-haloalkyl, nitro, cyano, $C_1$–$C_4$ alkylamino, diloweralkylamino $C_1$–$C_4$ alkylsulfonyl group, or phenyl optionally substituted with one $C_1$–$C_4$ alkyl, $C_1$–$C_4$ alkoxy or halogen; and, when taken together, Y and Z may form a ring in which YZ are represented by the structure: —$(CH_2)_n$—, where n is an integer selected from 3 and 4, provided that X is hydrogen; and when W is O and A is CN, $CH_3$ or $COOR_3$, provided that $R_3$ cannot be unsaturated alkyl and Y and Z cannot be alkylamino, dialkylamino or alkylthio, and the N-oxides thereof, and when $R_1$ and $R_2$ are not the same, the optical isomers thereof, and, except when $R_3$ is a salt-forming cation, the acid addition salts thereof.

Preferred compounds for use as sucrose enhancing agents for sugarcane are those represented by formula I wherein $R_1$ is methyl; $R_2$ is methyl, ethyl, isopropyl or cyclopropyl; W is oxygen; B is hydrogen, CO-alkyl $C_1$–$C_6$ or CO-phenyl optionally substituted with chloro, nitro or methoxy; A is $COOR_3$, $CH_2OH$ or CHO where $R_3$ is as described in formula I above, X is hydrogen, Y and Z are each selected from the group consisting of hydrogen, $C_1$–$C_6$ alkyl, $C_1$–$C_6$ alkoxy, halo, phenyl, nitro, cyano, trifluoromethyl or methylsulfonyl; and when Y and Z are taken together, YZ is —$(CH_2)_4$—.

A more preferred group of these 2-(2-imidazolin-2-yl)pyridines may be illustrated by the formula (Ia):

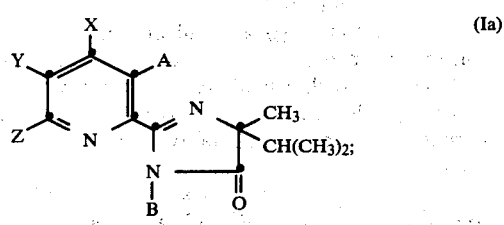

wherein B is hydrogen, CO-alkyl $C_1$–$C_6$ or CO-phenyl; A is $COOR_3$ where $R_3$ is as described in formula (I) above; X is hydrogen and Y and Z each represent hydrogen, $C_1$–$C_6$ alkyl, $C_1$–$C_4$-alkoxy, halo, $C_1$–$C_4$-haloalkyl, or phenyl and, when taken together, YZ represent —$(CH_2)_4$—.

The most preferred formula (Ia), 2,2-imidazolin-2-yl)pyridine compounds for use as sucrose enhancing agents for sugarcane are those wherein B, X, Y and Z are each hydrogen; A is $COOR_3$ and $R_3$ is hydrogen, alkyl $C_1$–$C_{12}$ optionally substituted with one alkoxy $C_1$–$C_3$ group or one benzyloxy group or one furyl group or one phenyl group, alkenyl $C_3$–$C_{12}$ optionally substituted with one $C_{1-C_3}$ alkyl group, alkynyl $C_3$–$C_{10}$ optionally substituted with one alkyl $C_1$–$C_2$ group; or a salt forming cation of alkali metals, alkaline earth metals, ammonium or lower aliphatic ammonium; and when $R_1$ and $R_2$ are not the same, the optical isomers and the isomeric mixtures thereof; and except when $R_3$ is hydrogen or a salt-forming cation, the acid addition salts thereof.

In accordance with the method of this invention the formula I 2-(2-imidazolin-2-yl)pyridine is applied to maturing sugarcane from about 2 weeks to about 4 weeks prior to first harvest, in the form of a liquid spray containing a sufficient amount of the formula I compound to provide from 0.16 kg/ha to about 4 kg/ha and preferably about 0.05 kg/ha to 2.0 kg/ha of said compound to said maturing cane.

In formulas I, and Ia above, alkali metals include: sodium, potassium and lithium, but sodium is generally preferred. Further, the term "organic ammonium," is defined as a group consisting of a positively charged nitrogen atom joined to from one to four aliphatic groups, each containing from one to 20 carbon atoms. Among the organic ammonium groups which are illustrative for the preparation of the aliphatic ammonium salts of the formula (I) imidazolinyl nicotinic acids and esters herein are: monoalkylammonium, dialkylammonium, trialkylammonium, tetraalkylammonium, monoalkenylammonium, dialkenylammonium, trialkenylammonium, monoalkynylammonium, dialkynylammonium, trialkynylammonium monoalkanolammonium, dialkanolammonium, trialkanolammonium, $C_5$-$C_6$-cycloalkylammonium, piperidinium, morpholinium, pyrrolidinium, benzylammonium and equivalents thereof. Exemplary of halogen hereinabove are chlorine, fluorine, bromine, and iodine, but chlorine and bromine are preferred.

In accordance with the process of the present invention, formula (I), 2-(2-imidazolin-2-yl)pyridine esters, wherein A is $COOR_3$ and $R_3$ represents a substituent other than hydrogen or a salt-forming cation, and $R_1$, $R_2$, X, Y and Z are as described above, can be prepared by reacting an imidazopyrrolopyridinedione, represented by formula (III), hereinbelow, with an appropriate alcohol and corresponding alkali metal alkoxide at a temperature ranging between about 20° C. and about 50° C.

In these reactions, the alcohol can function both as reactant and solvent. As such, a secondary solvent is not required. However, when an expensive alcohol is employed in the reaction, a less expensive secondary solvent, such as dioxane, tetrahydrofuran or other non-protic solvent, may be added to the reaction mixture. The amount of non-protic solvent added to the reaction mixture may be widely varied.

The overall reaction can be graphically illustrated as follows:

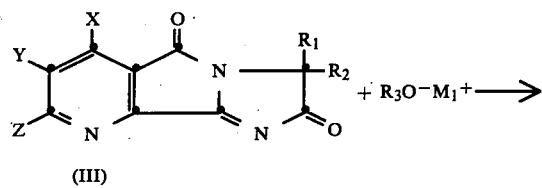

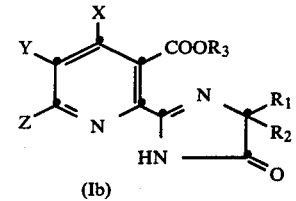

where $M_1$ is an alkali metal, and X, Y, Z, $R_1$, $R_2$ and $R_3$ are as above defined.

Advantageously, the formula (Ib) 2-(2-imidazolin-2-yl)pyridine esters can also be prepared from a formula (IV) dioxopyrrolopyridine acetamide, wherein $R_1$, $R_2$, X, Y and Z are as described above, by cyclization thereof with a strong base, such as 1,5-diazabicyclo[5.4.-0]undec-5-ene (DBU), in the presence of an inert organic solvent such as xylene or toluene to give the crude imidazopyrrolopyridine of formula (III). The reaction mixture is heated to a temperature between 100° C. and 150° C., and water is removed from the reaction mixture during the reaction using any convenient means, e.g., a Dean-Stark water separator. At least one equivalent of alcohol, represented by the formula (V) R₃OH, wherein R₃ represents a member other than hydrogen or a salt-forming cation, and $R_1$, $R_2$, X, Y and Z are as hereinabove described, is then added to the reaction mixture and the thus prepared mixture heated to reflux at a temperature between 100° C. and 150° C. to yield the formula (Ib) 2-(2-imidazolin-2-yl)pyridine ester. The overall reaction can be graphically illustrated as follows:

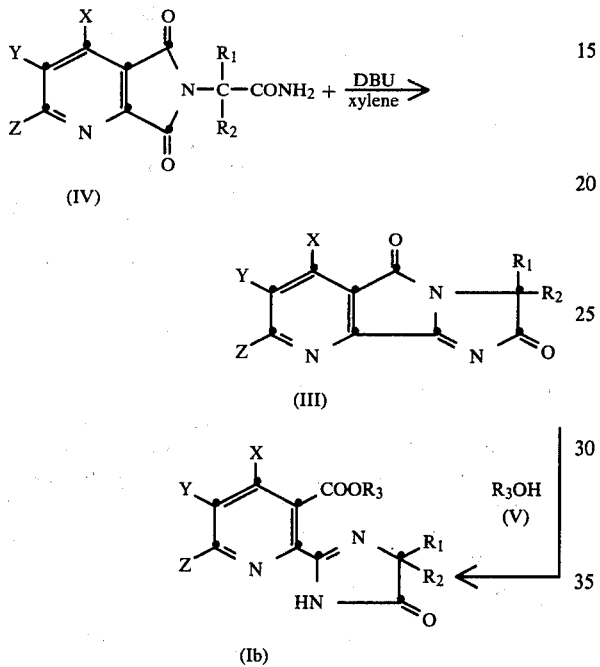

wherein X, Y, Z, $R_1$, $R_2$ and $R_3$ are as described above.

In still another embodiment relating to the preparation of the formula (Ib) 2-(2-imidazolin-2-yl)pyridine esters, the cyclization of a carbamoyl nicotinic acid ester, represented by formula (VI), with phosphorus pentachloride at an elevated temperature, generally between about 60° C. and 100° C. occurs. The reaction is preferably conducted in the presence of an inert organic solvent, such as toluene or benzene. Good yields of the hydrochloride salt of the desired formula (Ib) ester are attained. The hydrochloride salt is then readily converted to the formula (Ib) ester by dissolution of the acid addition salt in water and neutralization of the thus-prepared solution with base, such as sodium or potassium carbonate. The overall reactions can be illustrated as follows:

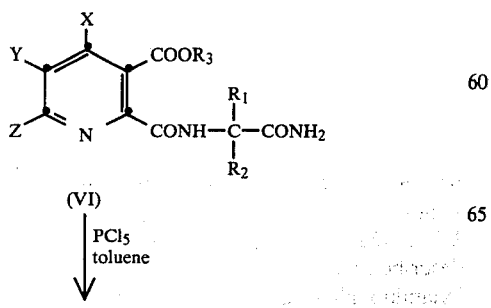

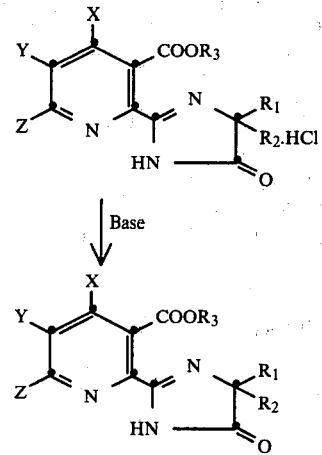

wherein A is COOR₃ and $R_3$ is a substituent other than hydrogen or a salt-forming cation, and $R_1$, $R_2$, X, Y and Z are as hereinabove described.

In still another embodiment for the preparation of the formula (Ib) 2-(2-imidazolin-2-yl)pyridines esters of the present invention, the cyclization of a carbamoyl nicotinic acid ester represented by formula (VI) using a mixture of phosphorus pentachloride and phosphorus oxychloride is accomplished. The reaction mixture is stirred at room temperature from about four to eight hours and then the POCl₃ removed in vacuo. The remaining residue is dispersed in an organic solvent such as toluene. The solvent is removed and the residue dispersed in water and heated to between 80° C. and 100° C. After cooling, the pH of the aqueous mixture is adjusted to 5-6 with sodium bicarbonate, and the product extracted into methylene chloride to give the desired formula (Ib) 2-(2-imidazolin-2-yl)pyridine ester. The reaction can be graphically illustrated as follows:

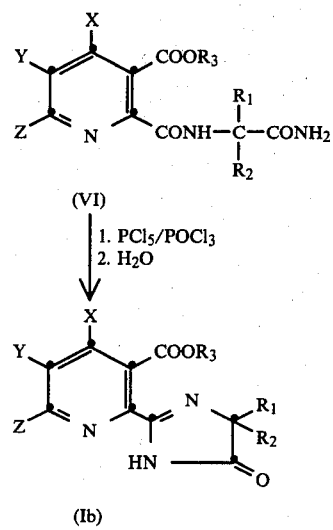

where A is COOR₃ and $R_3$ is a substituent other than hydrogen or a salt-forming cation, and $R_1$, $R_2$, X, Y and Z are as described above.

The formula (Ib) 2-(2-imidazolin-2-yl)pyridine ester in which A is COOR₃ and $R_3$ is alkyl $C_1$-$C_{12}$, alkenyl $C_3$-$C_{12}$, alkynyl $C_3$-$C_{10}$, cycloalkyl $C_3$-$C_6$ or the substituted derivatives of these groups and X, Y, Z, $R_1$ and $R_2$ are as described above, may be converted to the corresponding amide where A is $CONH_2$ by reaction with ammonia under superatmospheric pressure at a temperature between about 25° C. and 125° C. This reaction can be conducted in a protic solvent such as a lower alkanol or an aprotic solvent such as tetrahydrofuran, dioxane or the like. Likewise, using similar conditions but substituting hydroxylamine for ammonia in the above reaction yields the hydroxamic acid. These reactions may be graphically illustrated as follows:

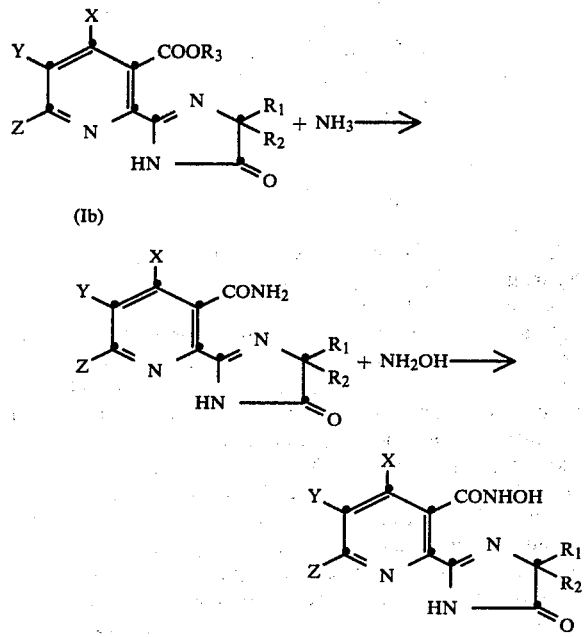

(Ib)

Treatment of the thus prepared primary amide described above with titanium tetrachloride and triethylamine, preferably in the presence of an inert aprotic solvent, such as tetrahydrofuran yields the corresponding nitrile. The reaction is generally conducted under a blanket of inert gas, such as nitrogen, at a temperature between about 0° C. and 10° C. The reaction may be illustrated as follows:

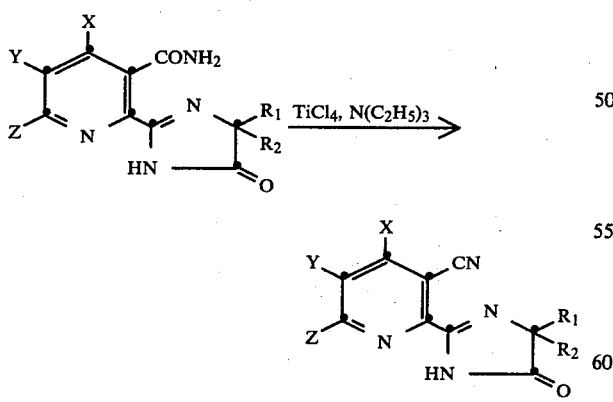

where X, Y, Z, $R_1$ and $R_2$ are as described above.

Preparation of the formula (VIII) N-substituted imidazolinone derivatives, wherein B is $COR_4$ or $SO_2R_5$; and A is $CH_3$, CN or $COOR_3$; and W is O; and $R_1$, $R_2$, $R_3$, X, Y and Z are as described above, excepting that Y and Z cannot be alkylamino, hydroxy or hydroxyloweralkyl; can be achieved by reaction of the appropriately substituted formula (I) 2-(2-imidazolin-2-yl)pyridine with an excess of acyl halide, acyl anhydride, or sulfonyl halide, alone or in a solvent such as pyridine or toluene at an elevated temperature between about 50° C. and 125° C. The reaction can be graphically illustrated as follows:

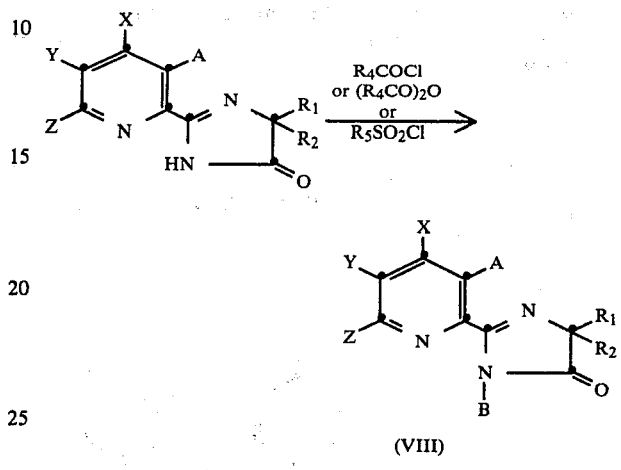

(VIII)

where A is $CH_3$, CN or $COOR_3$; $R_1$, $R_2$, $R_3$, $R_4$, $R_5$, X, Y and Z are as described above excepting that Y and/or Z cannot be alkylamino, hydroxyl, hydroxyloweralkyl.

Reaction of either the formula (I) 2-(2-imidazolin-2-yl)pyridine or the formula (VIII) N-substituted imidazolinone derivatives, described and illustrated immediately above, wherein A is $CH_3$, CN or $COOR_3$ provided that $R_3$ is as described above, excepting that it cannot be an unsaturated alkyl group, B is $R_4CO$ or $R_5SO_2$ and Y or Z cannot be alkylamino, alkylthio or dialkylamino; with an excess of m-chloroperbenzoic acid in the presence of an inert solvent such as methylene chloride, at refluxing temperature, yields the N-oxide corresponding to the pyridine derivative utilized as starting material. The reaction may be illustrated as follows:

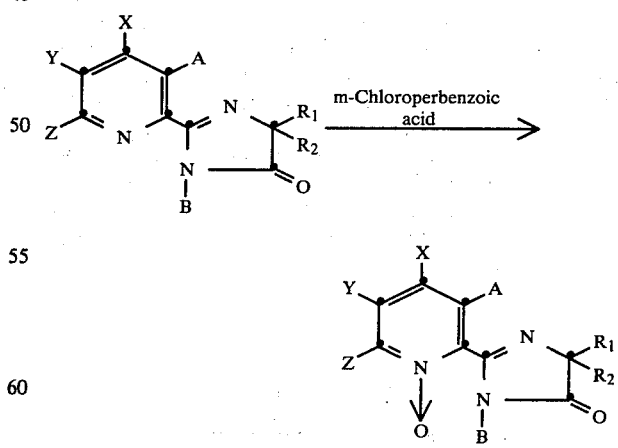

wherein A is $CH_3$, CN or $COOR_3$ is as described above excepting that $R_3$ cannot be an unsaturated alkyl group; B is $COR_4$ or $SO_2R_5$, $R_1$, $R_2$, $R_4$, $R_5$, X, Y and Z are as described above excepting that Y and Z cannot be alkylamino, alkylthio or dialkylamino.

Hydrolysis of the thus prepared N-oxide using a strong base such as sodium hydroxide in a lower alcohol yields the corresponding N-oxide in which B is H.

Advantageously, formula (I) esters in which B is hydrogen; W is oxygen and A is $COOR_3$ wherein $R_3$ is a saturated $C_1$–$C_{12}$ alkyl, $C_3$–$C_6$ cycloalkyl or benzyl substituent, and $R_1$, $R_2$, X, Y and Z are as defined above; can be prepared by reaction of the corresponding acid, i.e., where A is COOH, with an appropriate alcohol in the presence of a catalytic amount of a strong mineral acid such as hydrochloric acid, sulfuric acid or the like; at a temperature between about 50° C. and 100° C. The reaction may be illustrated as follows:

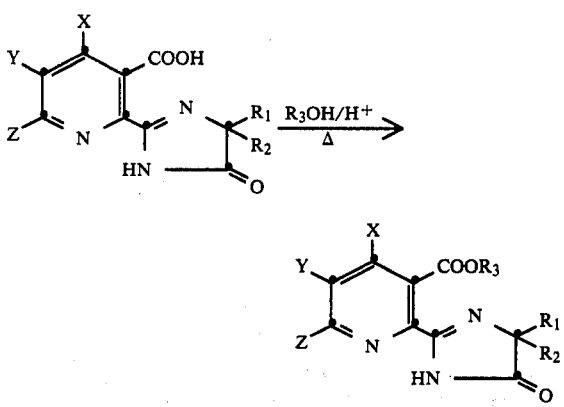

wherein $R_3$ is $C_1$–$C_{12}$ alkyl, $C_3$–$C_6$ cycloalkyl or benzyl; and $R_1$, $R_2$, X, Y and Z are as defined above.

The formula (I) acid as shown immediately above where A is COOH; B is hydrogen; W is oxygen and $R_1$, $R_2$, X, Y and Z are as defined above, is also readily converted to the corresponding methyl ester by reaction with diazomethane at a temperature between about B 0° C. and 25° C. The thus prepared methyl ester may then be reacted with an alkali metal alkoxide such as a sodium or potassium alkoxide, for convenience shown as $R_3ONa$, and an appropriate alcohol represented by the structure $R_3OH$, wherein $R_3$ is $C_1$–$C_{12}$ alkyl optionally substituted with one $C_1$–$C_3$ alkoxy, $C_3$–$C_6$ cycloalkyl, benzyloxy, furyl, phenyl, halophenyl, loweralkylphenyl, loweralkoxyphenyl, nitrophenyl or cyano; $C_3$–$C_{12}$ alkenyl optionally substituted with one or two $C_1$–$C_3$ alkoxy, phenyl or halogen groups; $C_3$–$C_6$ cycloalkyl optionally substituted with one or two $C_1$–$C_3$ alkyl groups or with $C_3$–$C_{10}$ alkynyl optionally substituted with one or two $C_1$–$C_3$ alkyl groups. The above reactions may be illustrated as follows:

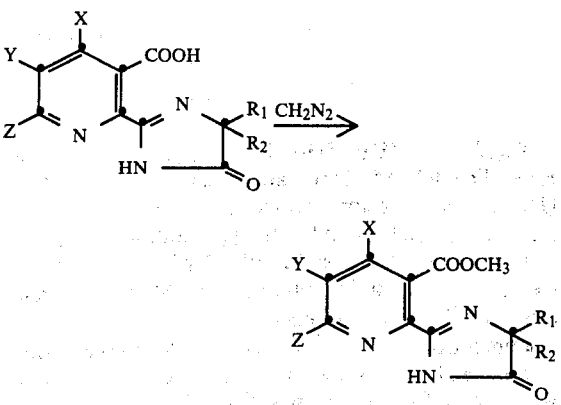

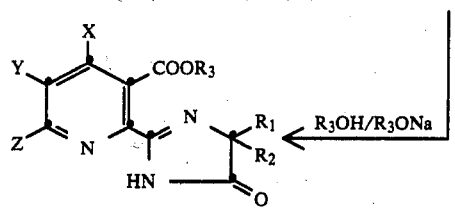

wherein $R_1$, $R_2$, $R_3$, X, Y and Z are as defined above.

Conversion of the above-identified formula (I) esters to their corresponding acid addition salts is readily achieved by treatment of said esters with strong acids, particularly strong mineral acids such as hydrochloric acid, sulfuric acid or hydrobromic acid.

Where the hydrohalide acid addition salts are desired, the formula (I) ester, wherein A is $COOR_3$ and $R_3$ is other than hydrogen or a salt-forming cation, and $R_1$, $R_2$, X, Y and Z are as described above, is dissolved in an organic solvent such as methylene chloride, chloroform, ether or the like. Addition of at least one equivalent of acid to the thus-prepared solution then yields the desired acid addition salt. The reaction may be illustrated as follows:

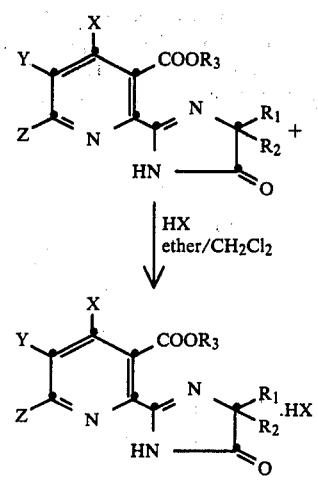

When the sulfuric acid salt of the ester is desired, the formula (I) ester is generally dissolved in a lower aliphatic alcohol such as methanol, ethanol, isopropanol or the like or mixtures of the above with water. Treatment of the mixture with at least one equivalent of sulfuric acid yields the sulfuric acid addition salt of the formula (I) ester.

In a further embodiment of the invention, the formula (I) compounds, wherein A is $COOR_3$ and $R_3$ is hydrogen and $R_1$, $R_2$, X, Y and Z, are as defined above, except that X, Y and Z cannot be $NO_2$ or halogen, can be prepared by hydrogenolysis of the benzyl ester of the imidazolinyl pyridine shown in formula (XV), wherein $R_1$, $R_2$, X, Y and Z, are as above-defined employing a palladium or platinum catalyst. In this reaction, the formula (XV) benzyl ester is dissolved or dispersed in an organic solvent, such as lower alcohol, an ether such as dioxane, tetrahydrofuran or the like, toluene or xylene. The catalyst, preferably palladium on a carbon carrier, is added to the mixture and the mixture heated to between 20° C. and 50° C. The heated mixture is then treated with hydrogen gas to yield the desired acid. The reaction may be graphically illustrated as follows:

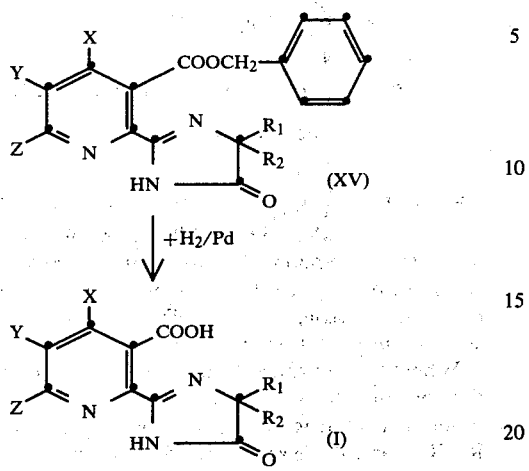

Alternatively, the formula (I) acids where A is COOH may be prepared by treatment of an aqueous solution of the formula (I) ester with a strong base. In practice the formula (I) ester is generally treated with one equivalent of base in aqueous solution, and the mixture heated to between 20° C. and 50° C. The mixture is then cooled and adjusted to pH 6.5 to 7.5 and preferably pH 7, with a strong mineral acid. Such treatment yields the desired acid. The reaction can be illustrated as follows:

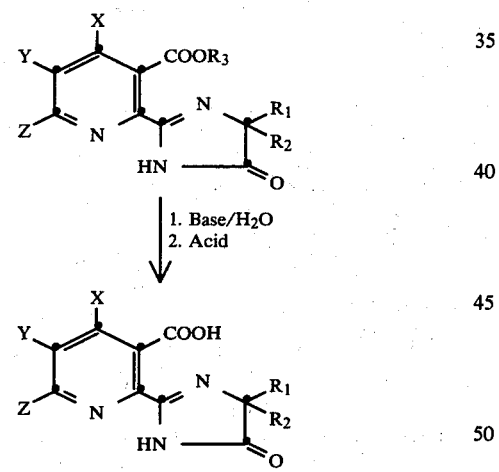

where $R_3$ is other than hydrogen or a salt-forming cation, and $R_1$, $R_2$, X, Y and Z are as described with reference to formula (I).

The formula (I) acids wherein A is COOH; B is hydrogen; W is oxygen and X, Y, Z, $R_1$ and $R_2$ are as described, can be prepared by reaction of the appropriately substituted formula (XVIII) imidazolinone with alkyl lithium, preferably in the presence of an inert solvent such as tetrahydrofuran under a blanket of nitrogen at a temperature between about −70° C. and −80° C. The thus-formed mixture is then treated with hexamethylphosphoramide and carbon dioxide preferably in an inert solvent such as tetrahydrofuran, to yield the desired product. Where it is desirable to obtain the formula (I) pyridine derivatives in which A is $CH_3$ and X, Y, Z, $R_1$ and $R_2$ are as stated above, the formula (XVIII) imidazolinone is treated in the same manner as described for the preparation of the acid, excepting that methyl iodide is substituted for the carbon dioxide. If dimethylformamide is substituted for the methyl iodide, the corresponding formyl derivatives are obtained. These reactions may be illustrated as follows:

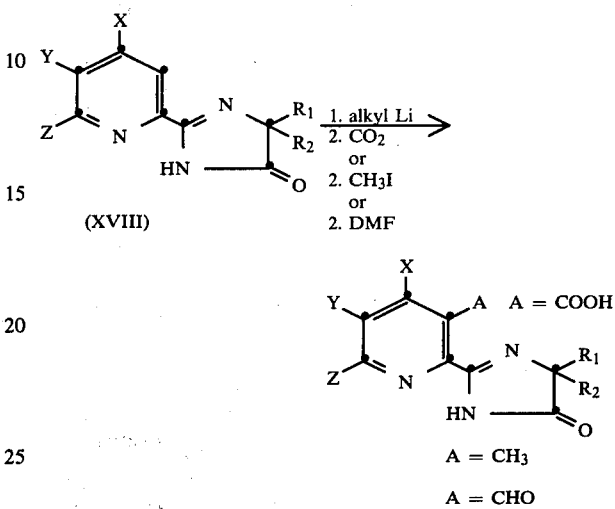

Advantageously, the formula (I) acids may be converted to the formula (VII) 5-H-imidazo[1′,2′:1,2]-pyrrolo[3,4-b]pyridine-3(2H),5-diones by reaction with dicyclohexylcarbodiimide (DCC). The reaction is preferably conducted using approximately an equimolar amount of the carbodiimide in the presence of a chlorinated hydrocarbon solvent at a temperature between about 20° C. to 32° C. The reaction may be graphically illustrated as follows:

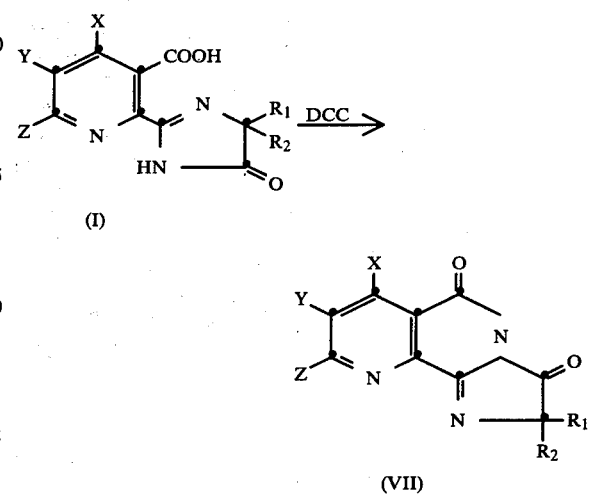

The formula (VII) 5H-imidazo[1′,2′:1,2]pyrrolo-[3,4-b]pyridine-3(2H),5-diones are isomers of the formula (III) imidazopyrrolopyridinediones referred to above, and are especially useful in the preparation of a variety of the formula (I) 2-(2-imidazolin-2-yl)-pyridine derivatives of the present invention, as will become apparent from the following discussion.

In practice, it is found that the formula (VII) 3(2H),5-diones can be reacted with at least one equivalent of an appropriate formula (V) $R_3OH$ alcohol in the presence of triethylamine as catalyst to yield the formula (I) pyridine ester corresponding to the alcohol used. The reaction is preferably conducted at a temperature between about 20° C. and 50° C. in the presence of an inert aprotic solvent, such as tetrahydrofuran, dioxane or the like. The reaction may be illustrated as follows:

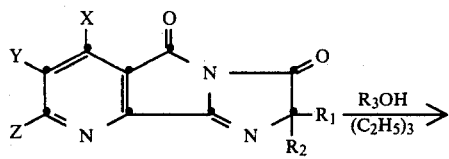

(VII)

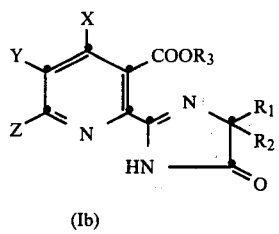

(Ib)

wherein $R_3$ represents a substituent as described above, excepting that hydrogen and salt-forming cations are excluded, and $R_1$, $R_2$, X, Y and Z, are as described above.

The formula (VII) 3(2H),5-diones are also readily converted to the formula (Ib) 2-(2-imidazolin-2-yl)-pyridine derivatives wherein $R_1$, $R_2$, X, Y and Z, are as described above; W is oxygen; B is hydrogen, and A is acetyl, benzoyl, trimethylphosphonoacetate or hydroxymethyl; by reaction thereof with methyl magnesium bromide, phenyl lithium, sodium trimethyl phosphonoacetate or sodium borohydride; respectively. The methyl magnesium bromide, phenyl lithium and sodium trimethylphosphonoacetate reactions are preferably carried out at a temperature between about −50° C. and −80° C., in the presence of an inert solvent such as tetrahydrofuran or dioxane under a blanket of inert gas, such as nitrogen. Reaction of the above-said formula (VII) diones with sodium borohydride is relatively mild. The reaction does not require a blanket of inert gas and can be conducted at temperatures between about −10° C. and +15° C.

Reaction of the formula (VII) diones with at least one equivalent of acetone oxime yields the acetone oxime ester of the formula (I) 2-(2-imidazolin-2-yl)pyridine where A is COON=C(CH$_3$)$_2$, B is hydrogen and $R_1$, $R_2$, X, Y and Z, are as described for formula (I) pyridine derivatives. The above reaction is generally conducted in the presence of an inert organic solvent such as toluene, benzene, xylene or the like at a temperature between about 40° C. and 80° C.

The above reactions are graphically illustrated below:

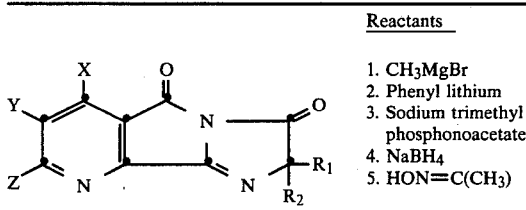

| Reactants |
|---|
| 1. CH$_3$MgBr |
| 2. Phenyl lithium |
| 3. Sodium trimethyl phosphonoacetate |
| 4. NaBH$_4$ |
| 5. HON=C(CH$_3$) |

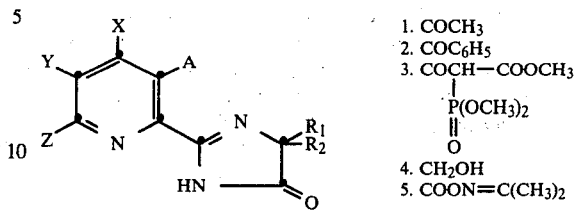

| A in Formula I |
|---|
| 1. COCH$_3$ |
| 2. COC$_6$H$_5$ |
| 3. COCH—COOCH$_3$<br>   \|<br>   P(OCH$_3$)$_2$<br>   \|\|<br>   O |
| 4. CH$_2$OH |
| 5. COON=C(CH$_3$)$_2$ | wherein $R_1$, $R_2$, X, Y and Z are as described above.

Formula (I) compounds, wherein A is COOR$_3$ and R$_3$ represents a salt-forming cation such as an alkali metal, alkaline earth metal, ammonium or aliphatic ammonium and $R_1$, $R_2$, X, Y and Z are as described above, can be prepared by dissolving the formula (I) 2-(2-imidazolin-2-yl)pyridine acid in an appropriate solvent and, thereafter, treating the solution of the acid with one equivalent of salt-forming cation. For compounds in which the salt-forming cation is an inorganic salt such as sodium, potassium, calcium, barium or the like, the formula (I) acid may be dissolved or dispersed in water or a lower alcohol or mixtures thereof. One equivalent of the salt-forming cation generally in the form of the hydroxide, carbonate, bicarbonate or the like, but preferably as the hydroxide, is admixed with the solution of the formula (I) acid. After several minutes, the formula (I) compound, wherein R$_3$ is the inorganic salt-forming cation, generally precipitates and can be recovered from the mixture by either filtration or through azeotropic distillation with an organic solvent such as dioxane.

To prepare the formula (I) compound in which A is COOR$_3$ and R$_3$ is ammonium or organic ammonium, the formula (I) acid is dissolved or dispersed in an organic solvent such as dioxane, tetrahydrofuran or the like, and the mixture treated with one equivalent of ammonia or the amine or the tetralkylammonium hydroxide. Among the amines which may be used in the above-said reaction are: methylamine, ethylamine, n-propylamine, isopropylamine, n-butylamine, isobutylamine, sec-butylamine, n-amylamine, iso-amylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoamylamine, dihexylamine, diheptylamine, dioctylamine, trimethylamine, triethylamine, tri-n-propylamine, triisopropylamine, tri-n-butylamine, triisobutylamine, tri-sec-butylamine, tri-n-amylamine, ethanolamine, n-propanolamine, isopropanolamine, diethanolamine, N,N-diethylethanolamine, N-ethylpropanolamine, N-butylethanolamine, allylamine, n-utenyl-2-amine, n-pentenyl-2-amine, 2,3-dimethylbutenyl-2-amine, dibutenyl-2-amine, n-hexenyl-2-amine, propylenediamine, tallowamine, cyclopentylamine, cyclohexylamine, dicyclohexylamine, piperidine, morpholine, and pyrrolidine. Among tetralkylammonium hydroxides contemplated methyl, tetraethyl, trimethyl-benzylammonium hydroxides. In practice, after several minutes, the ammonium or organic ammonium salt precipitates and can be separated from the solution by any convenient means, as by filtration or centrifugation. Additionally, the reaction mixture may be concentrated, and the remaining solvent removed with hexane, and the residue then dried to recover the ammonium or organic ammonium formula (I) salt. The above reactions may be graphically illustrated as follows:

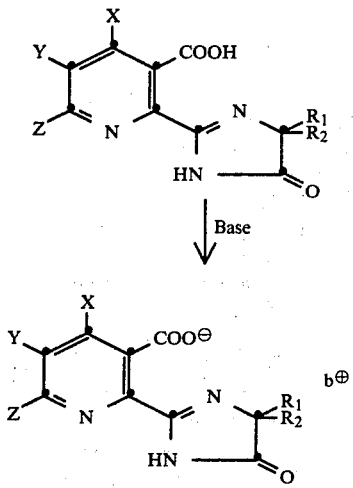

wherein $R_1$, $R_2$, X, Y and Z are as described above, and b is the salt forming cation.

When $R_1$ and $R_2$ represent different substituents, the carbon to which $R_1$ and $R_2$ are attached is an asymmetric center, and the products (as well as their intermediates) exist in d- and l- forms as well as dl-forms.

It should also be understood that the 2-(2-imidazolin-2-yl)pyridines and quinolines represented by formula (I) in which B=H may be tautomeric, while for convenience, they are depicted by a single structure identified as formula (I), they may exist in either of the isomeric forms illustrated as follows:

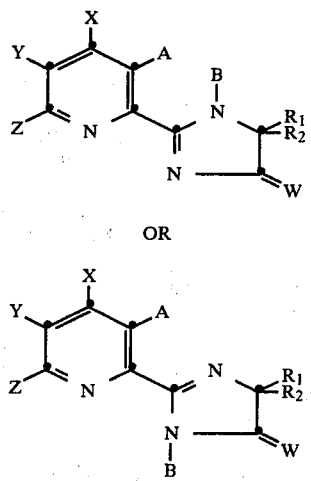

wherein A, W, X, Y, Z, $R_1$ and $R_2$ are as hereinabove defined and B is H. As such, both isomeric forms of the 2-(imidazolin-2-yl)pyridines and 2-(2-imidazolin-2-yl)quinolines are meant to be included under the formula (I) definitions.

One general method for the preparation of the formula (I) compounds involves the reaction of a quinolinic anhydride of formula (XVI) hereinbelow, with an appropriately substituted α-aminocarbonitrile of formula (XVII), hereinbelow, to yield a mixture of the monoamides of quinolinic acid of formula (IX) and formula (X).

This reaction is carried out at a temperature between about 20° C. and 70° C. and preferably between about 35° C. and 40° C. in an inert solvent, such as tetrahydrofuran, methylene chloride, ether, chloroform, toluene or the like. The thus-formed acids are then cyclized to the corresponding pyrrolopyridine acetonitrile, depicted by formula (XI), by heating the reaction mixture with an excess of acetic anhydride in the presence of a catalytic amount of sodium acetate or potassium acetate.

In general, the above reaction is carried out by treating the reaction mixture with acetic anhydride, acetyl chloride, thionyl chloride or the like and heating said mixture to a temperature between about 20° C. and 100° C. Hydration of the thus-formed pyrrolopyridine acetonitrile formula (XI) is carried out by treating said acetonitrile with a strong acid such as sulfuric acid. This reaction yields the formula (XII) pyrrolopyridine acetamide. Although the addition of a nonmiscible solvent such as methylene chloride, chloroform or the like is not essential to the conduct of the above described reaction, addition of such a solvent to the reaction mixture is generally preferred. Said reaction is usually carried out at a temperature between about 10° C. to 70° C.

The cyclization of the formula (XII), hereinbelow, pyrrolopyridine acetamide yields the tricyclic formula (III) imidazopyrrolopyridinediones which are intermediates for the imidazolinyl nicotinic acids and esters of the present invention referred to above and represented by formula (Ib).

The product of this reaction is predominantly the desired imidazopyrrolopyridinedione (85%) together with the isomer of formula (IIIa). Mixtures of this ratio of the two isomers generally give substantially isomerically pure nicotinate product.

The cyclization reaction is preferably conducted at a temperature of from 80° C. to 150° C. in the presence of a base such as sodium or potassium hydride or an acid such as an aromatic sulfonic acid and a solvent which will form an azeotropic mixture with water, permitting virtually immediate removal thereof from the reaction mixture as it is formed. Among the solvents which may be employed are toluene, benzene, xylenes and cyclohexane. Bases which may be used include alkali metal hydroxides, alkali metal hydrides, alkali metal oxides, tertiary amines such as diisopropyl ethylamine, 1,5-diazabicyclo[3.4]nonene-5,1,5-diazobicyclo[5.4.0]-undecene-5,1,4-diazabicyclo[2.2.2]octane, tetramethylguanidine, potassium fluoride and quaternary ammonium hydroxide, such as trimethylbenzyl ammonium hydroxide and strongly basic ion exchange resins.

Finally, acidic reagents which can be employed herein include aromatic sulfonic acids, such as p-toluenesulfonic acid, β-naphthalenesulfonic acid, naphthalenedisulfonic acid, and the like.

The mixture of compounds of formula (III) and formula (IIIa) is then converted to formula (Ib), as discussed above, with an alkali metal alkoxide and alcohol.

The above reactions are graphically illustrated on Flow Diagram I below, when X, Y, Z, $R_1$, $R_2$ and $R_3$ are as defined above.

FLOW DIAGRAM I

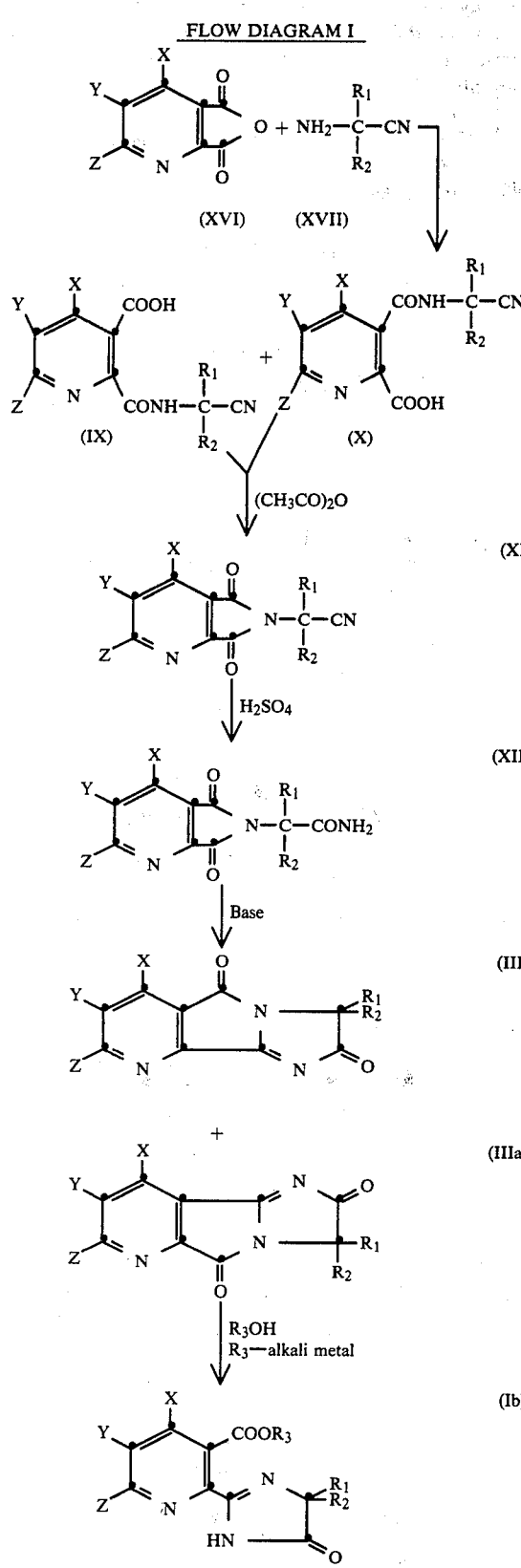

bly in a ketonic solvent such as acetone under a blanket of nitrogen to yield an isomeric mixture of the formula (XX) and formula (XXI) acids. The mixture is then treated with acetic anhydride and a catalytic amount of sodium acetate at an elevated temperature to give the dihydrodioxopyrrolopyridine acid formula (XXII). Reaction of the thus-formed acid with a thionyl halide, such as thionyl chloride or thionyl bromide, in the presence of an organic solvent such as toluene, xylene, benzene or the like, at an elevated temperature, i.e., 80° C. to 150° C., gives the formula (XXIII) acid halide corresponding to the formula (XXII) acid. Treatment of this acid halide with excess ammonia then yields the formula (IV) dihydrodioxopyrrolopyridine acetamide. The reaction is preferably carried out in the presence of an aprotic solvent.

Reaction of the formula (IV) acetamide with 1,8-diazabicyclo[5,4,0]undec-7-ene in an inert organic solvent such as toluene or xylene at an elevated temperature between about 80° C. and 125° C. gives the formula (III) imidazopyrrolopyridinedione which may be heated with morpholine or an appropriate $NH_2R_6$ amine to yield the 2-(2-imidazolin-2-yl)nicotinamides. These reactions are illustrated as Flow Diagram II.

FLOW DIAGRAM II

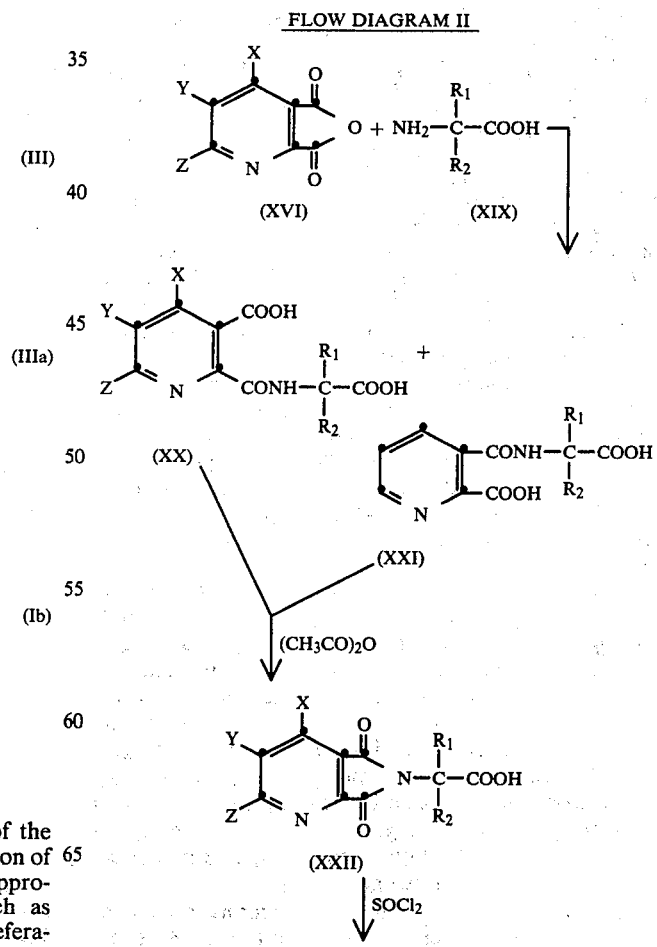

Another general method for the preparation of the formula (I) pyridine derivatives involves the reaction of a quinolinic anhydride of formula (XVI), with an appropriately substituted α-aminocarboxylic acid such as α-methylvaline represented by formula (XIX), prefera- -continued
FLOW DIAGRAM II

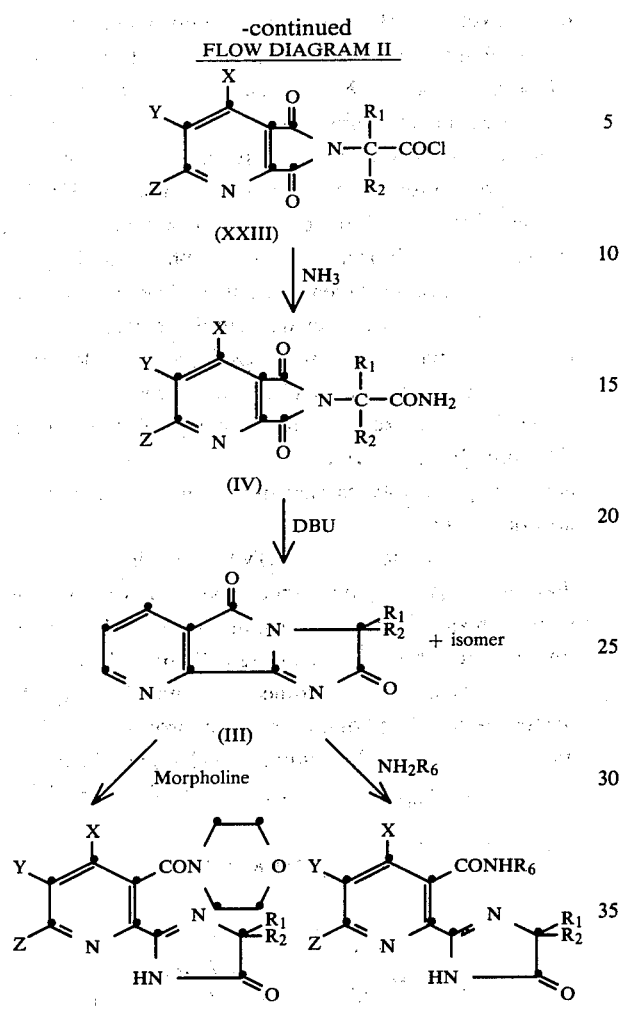

In another general procedure, the 2-(2-imidazolin-2-yl)pyridine acids and esters of formula (I), can be prepared by reacting the 2-carboalkoxynicotinoyl chloride of formula (XIV), hereinbelow, preferably as the methyl ester and preferably in the form of the hydrochloride salt, with the appropriate aminocarboxamide depicted by formula (XIII). The reaction yields the carbamoyl picolinate, formula (XV), and is preferably carried out in an inert blanket of gas such as nitrogen. The reaction mixture is generally maintained at a temperature below 30° C. during the reaction period.

The thus-formed carbamoyl picolinate, formula (XV), hereinbelow, can then be dispersed in an inert non-protic solvent such as xylene or toluene and heated to about 50° C. to 130° C. with 1,5-diazabicyclo-[5.4.0]undec-5-ene. The reaction yields a mixture of the formula (III) and formula (IIIa), imidazopyrrolopyridinedione isomers which can be used without separation in the following reaction, wherein the reaction mixture is treated with an alkali metal alkoxide, in the presence of an alcohol to yield a mixture of the imidazolinyl nicotinate and the imidazolinyl picolinate. The desired formula (Ib) nicotinate can be readily separated from the picolinate by neutralizing the reaction mixture, preferably with glacial acetic acid, concentrating the neutralized solution and chromatographing the resulting residue on silica gel in ether.

Conversion of the imidazolinyl nicotinate esters to the corresponding acids or acid addition salts can be readily achieved by the methods previously described. Similarly, the imidazolinyl nicotinic acids can be converted to the corresponding alkali metal, ammonium, or organic ammonium salts by the methods previously described.

Preparation of the formula (I) acids and esters, by the route described above, is graphically illustrated in Flow Diagram III below.

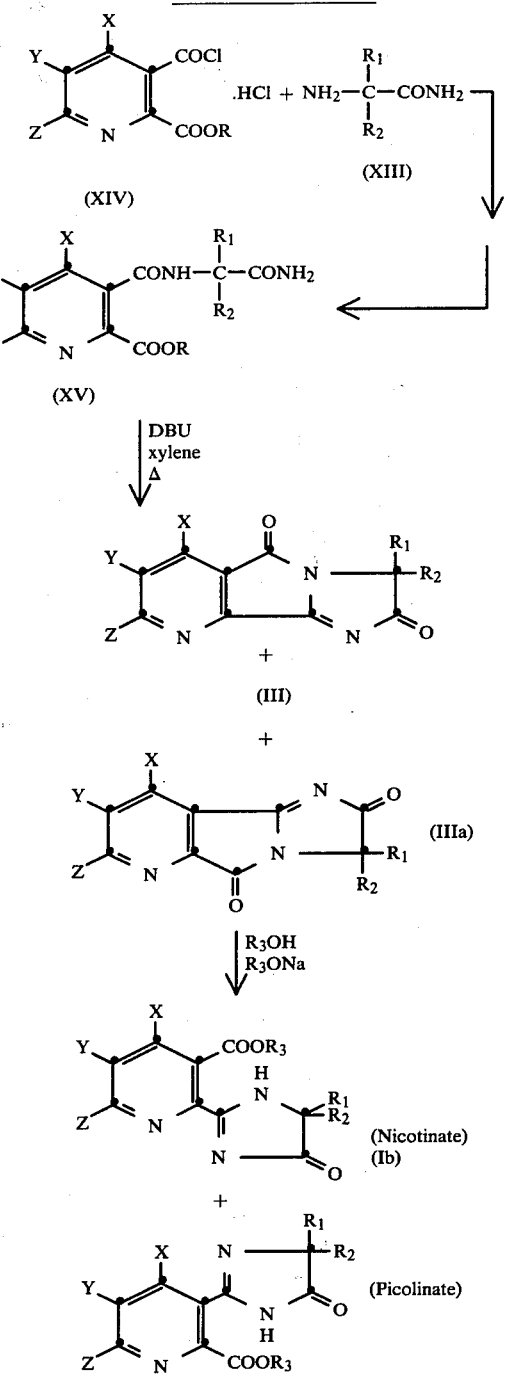

Advantageously, the formula I compounds of this invention can be formulated as solid or liquid compositions which may be dispersed in a liquid or solid diluent for application to sugarcane.

Since the formula I imidazolinyl pyridine derivatives, wherein $R_3$ is a salt forming cation, are water soluble these compounds can simply be dispersed in water an applied as a dilute aqueous spray to the foliage of sugarcane. These salts also lend themselves to formulation as flowable concentrates.

Wettable powders can be prepared by grinding together about 20% to 45% by weight of a finely divided carrier such as kaolin, bentonite, diatomaceous earth, attapulgite, or the like, 45% to 80% by weight of the active compound, 2% to 5% by weight of a dispersing agent such as sodium lignosulfonate, and 2% to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 5% to 25% by weight of the active ingredient in about 65% to 90% by weight of N-methylpyrrolidone, isophorone, butyl cellosolve, methylacetate or the like and dispersing therein about 5% to 10% by weight of a nonionic surfactant such as an alkylphenoxy polyethoxy alcohol. This concentrate is dispersed in water for application as a liquid spray.

As previously suggested, in the field the active ingredient is conveniently applied in the form of an aqueous solution or suspension, e.g., a liquid composition which may be sprayed from a boom spray. Generally, a sufficient amount of the wettable powder, emulsifiable concentrate flowable liquid or salt, is dispersed in enough water to provide a concentration of active pyridine derivative such that application of the suspension or emulsion at the rate of from about 70 to 200 liters of liquid composition per hectare, will provide from about 0.016 kg/ha to 4.0 kg/ha of the active pyridine derivative.

While the preferred diluent for the above-identified compositions is water, other non-phytotoxic diluents, such as mineral oils or mineral oil-in-water emulsions maybe used to achieve application of the pyridine derivative to the sugarcane. The concentration of non-ionic surfactant and/or dispersing agent in aqueous compositions containing the pyridine derivative is generally between 0.01% to 3% by weight.

In order to facilitate a further understanding of the invention, the following examples are presented primarily for the purpose of illustrating certain more specific details thereof. The invention is not be be deemed limited thereby except as defined in the claims. Unless otherwise noted, all parts are by weight.

EXAMPLE 1

Preparation of
5,7-Dihydro-α-isopropyl-α-methyl-5,7-dioxo-6H-pyrrolo[3,4-b]pyridine-6-acetonitrile To a stirred solution containing 212 g quinolinic anhydride in 950 ml methylene chloride is added at a moderate rate 167 g of 2-amino-2,3-dimethylbutyronitrile. The mixture had reached the boiling point of the solution after about one quarter of the aminonitrile had been added and the rate of addition is adjusted to maintain this temperature. After the addition the solution is heated under reflux for a further 4 hours. The solution is cooled, filtered and concentrated to a thick oil. This oil is dissolved in 950 ml acetic anhydride, 6 g anhydrous sodium acetate added and the mixture distilled until the vapor temperature reached 118° C. when the heating was continued under reflux for 3 hours. The mixture is concentrated in vacuo the residue dissolved in 500 ml toluene and again concentrated. This is repeated. The residue is slurried with a mixture of ether and hexane and the crude product which crystallizes collected (349 g). This is dissolved in 700 ml methylene chloride and filtered through a column containing 700 g silica gel and the product eluted with methylene chloride. Concentration of the eluant gave 258 g of the desired product. An analytically pure sample with mp 95°–96° C. can be obtained by the recrystallization of the product from ether-methylene chloride.

Using the appropriate amino nitrile and quinolinic anhydride in the above procedure, the following pyrrolopyridines are prepared:

| $R_1$ | $R_2$ | X | Y | Z | mp °C. |
|---|---|---|---|---|---|
| CH₃ | CH₃ | H | H | H | 119–123 |
| CH₃ | C₂H₅ | H | H | H | 95–97 |
| CH₃ | △ | H | H | H | 69–73 |
| CH₃ | CH₂CH(CH₃)₂ | H | H | H | oil |
| —(CH₂)₅— | | H | H | H | 85–87 |
| C₂H₅ | C₂H₅ | H | H | H | 71–72.5 |
| CH₃ | CH(CH₃)₂ | CH₃ | H | H | 129.5–131.3 |
| CH₃ | CH(CH₃)₂ | H | H | OCH₃ | 108–110 |
| CH₃ | CH(CH₃)₂ | H | H | Cl | 94–96 |

EXAMPLE 2

Preparation of
5,7-Dihydro-α-isopropyl-α-methyl-5,7-dioxo-6H-pyrrolo[3,4-b]pyridine-6-acetamide To 330 ml concentrated sulfuric acid is added portion wise with thorough stirring 298 g finely divided nitrile so that the temperature did not go about 72° C. After the addition the temperature is adjusted to 60°–65° C. and maintained there for 1½ hours. The mixture is cooled, quenched with ice and finally diluted to approximately 4 liters. After adding 454 g sodium acetate and cooling at 0° C. for 2 hours the mixture is filtered, the solids collected and washed twice with 500 ml water containing sodium acetate followed by water to remove all the sulfuric acid. The solid is dried to give 289 g of product, mp 176°–178° C. Material made in a smaller way and analytically pure had mp 188°–190° C.

Employing the appropriate pyrrolopyridineacetonitrile in the above procedure, the following pyrrolopyridineacetamides are prepared.

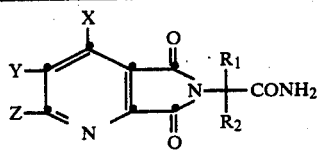

| R₁ | R₂ | X | Y | Z | mp °C. |
|---|---|---|---|---|---|
| CH₃ | CH₃ | H | H | H | 203-5 |
| CH₃ | C₂H₅ | H | H | H | 158-161 |
| CH₃ | △ | H | H | H | 195-198 |

EXAMPLE 3

Preparation of 3-Isopropyl-3-methyl-5H-imidazo[1',2';1,2]pyrrolo[3,4,6]pyridine-2-(3H), 5-dione A mixture of 50 g amide and 450 ml toluene is heated under a Dean-Stark water separator to remove traces of water. To the cooled mixture is added 10.1 g of a 50% suspension of sodium hydride in mineral oil and the mixture heated under reflux for 23 hours. The hot solution is filtered, concentrated in vacuo where upon the residue is crystallized. The mineral oil is removed by decantation and the solid washed with hexanes and dried in vacuo to give 45.5 g product which, by nmr analysis, is approximately 90% the desired isomer II and 10% the undesired isomer IIa.

A pure sample of isomer II can be obtained by recrystallizing the crude product from hexanemethylene chloride mp 107°-115° C.

The cyclisation can be achieved by either the basic reagent sodium and potassium hydroxide, or the acidic reagent p-toluenesulfonic acid in a toluene solvent. It should be understood that a mixture of products corresponding to Structures II and IIa above is obtained and in general these are not purified but used directly for the preparation of the desired nicotinic acid esters.

Employing the appropriate pyrrolopyridine carboxamide, the following imidazopyrrolopyridines are prepared.

| R₁ | R₂ | X | Y | Z | mp °C. |
|---|---|---|---|---|---|
| CH₃ | CH₃ | H | H | H | |
| CH₃ | C₂H₅ | H | H | H | |
| CH₃ | △ | H | H | H | |
| —CH—CH₂CH₂CH₂CH₂— (CH₃) | | H | H | H | 125-130 |
| CH₃ | CH(CH₃)₂ | H | H | OCH₃ | 147-147.5 |

EXAMPLE 4

Preparation of 3-Isopropyl-5-H-imidazo[2',2':1,2]pyrrolo[3,4-6]pyridine-2(3H)-dione A mixture containing 52 g of 3-[(1-Carbamoyl-1,2-dimethylpropyl)picolinate, 1.77 ml 1,5-diazabicyclo[5.4.0]-undec-5-ene(DBU) in 400 ml xylene is heated under reflux under a Dean-Stark water separator for 2 hours. The mixture is concentrated in vacuo and the residue is chromatographed on 400 g basic alumina. The mixture of desired products is eluted with methylene chloride and used without further purification.

EXAMPLE 5

Preparation of Methyl 2-(isopropyl-5-methyl-4-oxo-2-imidazolin-2-yl)nicotinate

To 20 ml dry methanol in which 10 mg sodium hydride had reacted is added 2.0 g of a mixture of the imidazopyrrolopyridines. After stirring for 16 hours, 0.03 g glacial acetic acid is added (to neutralize the base), the solution concentrated in vacuo and the residue chromatographed on silica gel in ether. The faster moving material, the desired ester, is obtained in several fractions, combined, concentrated and crystallized from acetonitrile to give the imidazolinyl nicotinate, mp 121°-123.5° C. An analytically pure sample crystallized from methylene chloride hexane exhibits a melting point of from 121°-122° C.

EXAMPLE 6

Preparation of Methyl 2-(5-isopropyl-5-methyl-4-oxo-2-imidazolin-yl)nicotinate

This method involves the formation of the tricyclic compounds of Example 3 and 4, without isolation, directly forming the nicotinic acid esters:

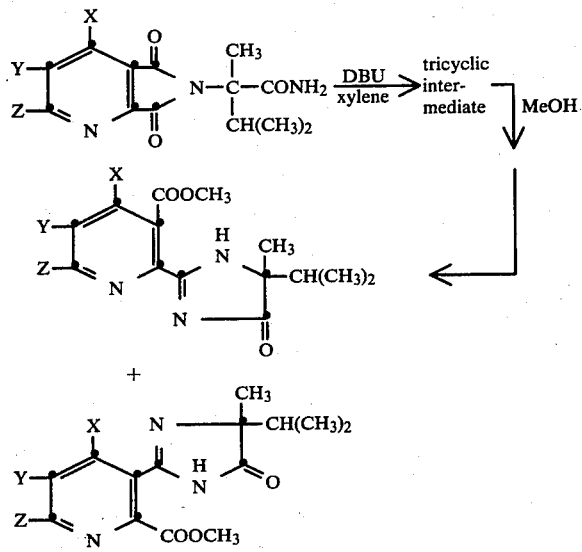

A mixture of 25 g amide and 1 ml 1,5-diaza-bicyclo-[5.4.0]undec-5-ene(DBU) in 500 ml xylene is heated under reflux for 1 hour under a Dean-Stark water separator. The mixture is cooled somewhat, the water separator removed, 100 ml anhydrous methanol added and the mixture heated under reflux for 1 hour. The solvents are then removed in vacuo and the product isolated by chromatography as described in Example 5 above to give 13.65 g product mp 120°–122° C. identical to that described in Example 5 above.

EXAMPLE 7

Preparation of Methyl 2-(5-isopropyl 5-methyl-4-oxo-2-imidazolin-2-yl)nicotinate. Method A (Flow Diagram)

A mixture of 13.65 g of the nicotinate and 9.69 g phosphorus pentachloride in 110 ml dry toluene is heated with stirring to 80° C. After 1½ hours, the thick mixture is cooled, filtered and the solid washed with ether and dried. This is the hydrochloride salt of the desired product.

This salt is dissolved in 60 ml water; neutralized with sodium bicarbonate, the resulting precipitate removed by filtration, washed with water and air-dried to give the product identical to that prepared by the procedure of Example 5.

Method B

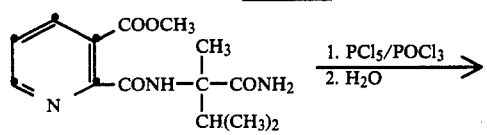

-continued
Method B

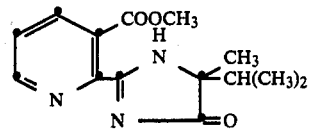

A mixture of 5.0 g nicotinate and 7.1 g phosphorus pentachloride in 40 ml phosphorus oxychloride is stirred at room temperature overnight. The phosphorous oxychloride is removed in vacuo, the residue suspended in 40 ml toluene and again concentrated. This is repeated. Water (40 ml) is added to the residue and the mixture heated to reflux and held there for 1 hour. After cooling, the mixture is extracted with methylene chloride, the extract dried and concentrated to give 1.05 g of the desired product. The pH of the aqueous phase from the methylene chloride extraction is adjusted to 5–6 with sodium bicarbonate solution and the mixture extracted again with methylene chloride. The dried extract was concentrated and the residue crystallized to give a further 2.65 g of the desired product identical to that described in Example 5.

The following nicotinic acid esters are prepared by one or more of the methods described above:

| $R_3$ | $R_1$ | $R_2$ | X | Y | Z | mp °C. |
|---|---|---|---|---|---|---|
| $CH_3$ | $CH_3$ | $C_2H_5$ | H | H | H | 126.5–128.5 |
| $CH_2{\equiv}CH$ | $CH_3$ | $CH(CH_3)_2$ | H | H | H | 104–106 |
| $CH_3$ | $-CH-(CH_2)_4-$ with $CH_3$ | | H | H | H | 151–155.3 |
| $CH_2C{\equiv}CH$ | $-CH-(CH_2)_4-$ with $CH_3$ | | H | H | H | 117–120 |
| $CH_2C_6H_5$ | $-CH-(CH_2)_4-$ with $CH_3$ | | H | H | H | 148.5–151.3 |
| $CH_2C{\equiv}CH$ | $CH_3$ | $CH_3$ | H | H | H | 171–173 |
| $CH_3$ | $CH_3$ | $CH_3$ | H | H | H | 148–150 |
| $CH_2C_6H_5$ | $CH_3$ | $CH_3$ | H | H | H | 142–144 |
| $CH_2C_6H_5$ | $CH_3$ | $C_2H_5$ | H | H | H | 118–120 |
| $CH_2C{\equiv}CH$ | $CH_3$ | $C_2H_5$ | H | H | H | 138–140 |
| $-C_{12}H_{25}-n$ | $CH_3$ | $CH(CH_3)_2$ | H | H | H | 55–57 |
| $-C_2H_5$ | $CH_3$ | $CH(CH_3)_2$ | H | H | H | 72–75 |
| $CH_2CH_2OCH_2C_6H_5$ | $CH_3$ | $CH(CH_3)_2$ | H | H | H | 90–92.5 |
| 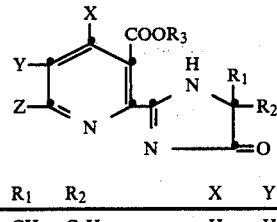 | $CH_3$ | $CH(CH_3)_2$ | H | H | H | 120.5–122 |
| $-CH(CH_3)_2$ | $CH_3$ | $CH(CH_3)_2$ | H | H | H | 94–97.5 |
| $-CH_2C_6H_5$ | $CH_3$ | $CH(CH_3)_2$ | H | H | H | 122–125 |
| $-CH_2-C{\equiv}C-C_7H_{15}-n$ | $CH_3$ | $CH(CH_3)_2$ | H | H | H | oil |
| $CH_2CH_2OCH_3$ | $CH_3$ | $CH(CH_3)_2$ | H | H | H | 60–63 |
| $CH_2CH{=}CH_2$ | $CH_3$ | $CH(CH_3)_2$ | H | H | H | 81–84 |

-continued

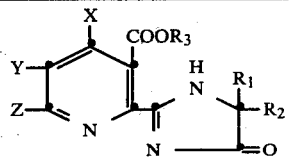

| R₃ | R₁ | R₂ | X | Y | Z | mp °C. |
|---|---|---|---|---|---|---|
| −CH(CH₃)−CH=CH₂ | CH₃ | CH(CH₃)₂ | H | H | H | oil |
| CH₂−C(CH₃)=CH₂ | CH₃ | CJ(CH₃)₂ | H | H | H | 98–100 |
| CH(CH₃)−C≡CH | CH₃ | CH(CH₃)₂ | H | H | H | oil |
| CH₂−CH=CHCH₃ | CH₃ | CH(CH₃)₂ | H | H | H | 87–89 |
| −C(CH₃)₃ | CH₃ | CH(CH₃)₂ | H | H | H | 124–126 |
| cyclohexyl | CH₃ | CH(CH₃)₂ | H | H | H | 95.5–98 |
| C₁₈H₃₇−n | CH₃ | CH(CH₃)₂ | H | H | H | 77.3–79.2 |
| CH₂C₆H₅ | CH₃ | CH(CH₃)₂ | H | H | H | 116.5–119 |
| −CH₂C₆H₅ | CH₃ | CH₂CH(CH₃)₂ | H | H | H | 76–78.5 |
| CH₃ | CH₃ | CH₂CH(CH₃)₂ | H | H | H | 92–94 |
| −C₄H₉−n | CH₃ | CH₂(CH₃)₂ | H | H | H | 54–57 |
| CH₂C≡CH | CH₃ | CHCH(CH₃)₂ | H | H | H | 128.5–131 |
| CH₃ | CH₃ | cyclopropyl | H | H | H | 128–131 |
| CH₂C₆H₅ | CH₃ | cyclopropyl | H | H | H | 111–113 |
| CH₃ | CH₃ | CH(CH₃)₂ | H | H | OCH₃ | 154–155 |
| CH₂−CH=CH−C₇H₁₅−n | CH₃ | CH(CH₃)₂ | H | H | H | oil |
| CH₂−C(Cl)=CH₂ | CH₃ | CH(CH₃)₂ | H | H | H | 73–77 |
| C₆H₁₃−n | CH₃ | CH(CH₃)₂ | H | H | H | oil |
| CH(CH₃)CH=CH−CH₃ | CH₃ | CH(CH₃)₂ | H | H | H | oil |
| CH₃ | −(CH₂)₅− | | H | H | H | 146–148 |
| CH₂CH=(CH₃)₂ | CH₃ | CH(CH₃)₂ | H | H | H | 77.5–79 |
| CH₂C₆H₅ | −(CH₂)₅− | | H | H | H | 117–122 |
| CH₂≡CCH₂OH | CH₃ | CH(CH₃)₂ | H | H | H | gum |
| CH₂C₆H₅ | C₂H₅ | C₂H₅ | H | H | H | 114.5–118 |
| C(CH₃)C≡CH | CH₃ | CH(CH₃)₂ | H | H | H | 128–132 |
| CH₂CH₂N⊕(CH₃)₃I⊖ | CH₃ | CH(CH₃)₂ | H | H | H | 165–175 |
| CH₃ | C₂H₅ | C₂H₅ | H | H | H | 132.5–135.5 |
| C(CH₃)₂C≡CH | CH₃ | CH(CH₃)₂ | H | H | H | 104–106 |
| CH₂C≡CH | CH₃ | cyclopropyl | H | H | H | 122–124 |
| CH₂C≡CH | −(CH₂)− | | H | H | H | 164.5–166.5 |
| CH₃ | CH₃ | CH(CH₃)₂ | CH₃ | H | H | 114–115.5 |
| CH₂C≡CH | C₂H₅ | C₂H₅ | H | H | H | 135.5–137 |
| CH₂−C₆H₄−OCH₃ | CH₃ | CH(CH₃)₂ | H | H | H | 111–113 |
| CH₂−C₆H₄−Cl | CH₃ | CH(CH₃)₂ | H | H | H | 136–138 |

-continued

[Structure: pyridine with X at 4-position, COOR3 at 3-position, Y at 5, Z at 6, N at 1; 2-position bears -N=C(-NH-CR1R2-C(=O)-) fused imidazolinone ring]

| R3 | R1 | R2 | X | Y | Z | mp °C. |
|---|---|---|---|---|---|---|
| CH2-C6H4-NO2 | CH3 | CH(CH3)2 | H | H | H | 131.5–133 |
| CH2COOCH3 | CH3 | CH(CH3)2 | H | H | H | 104–108 |
| CH2-CH(-O-)C(CH3)2(-O-)CH2 (dioxolane) | CH3 | CH(CH3)2 | H | H | H | 95–97 |
| CH2CH2CH2COOC2H5 | CH3 | CH(CH3)2 | H | H | H | oil |
| CH(CH3)COOCH3 | CH3 | CH(CH3)2 | H | H | H | 133–135 |
| CH3 | CH3 | CH(CH3)2 | H | Br | H | 122.5–126 |
| CH2CH=CH—COOC2H5 | CH3 | CH(CH3)2 | H | H | H | oil |
| (CH2)4COOCH3 | CH3 | CH(CH3)2 | H | H | H | oil |
| CH2-C6H4-C(CH3)3 | CH3 | CH(CH3)2 | H | H | H | 108–111 |
| CH2CH2-C6H5 | CH3 | CH(CH3)2 | H | H | H | 107–109 |
| CH2-C6H5 | CH3 | CH(CH3)2 | CH3 | H | H | 130–132 |
| CH2CH=CH-C6H5 | CH3 | CH(CH3)2 | H | H | H | 113–115 |
| CH2CH=C(CH3)— CH2CH2CH=C(CH3)2 | CH3 | CH(CH3)2 | H | H | H | oil |
| CH2CH(OH)CH2OH | CH3 | CH(CH3)2 | H | H | H | oil |
| (CH2)3C≡CH | CH3 | CH(CH3)2 | H | H | H | 73–75 |
| CH2CH2-(pinanyl, CH3,CH3) | CH3 | CH(CH3)2 | H | H | H | oil |
| CH(C6H5)COOCH3 | CH3 | CH(CH3)2 | H | H | H | oil |
| CH2CH2—C(CH3)=CH2 | CH3 | CH(CH3)2 | H | H | H | oil |
| (CH2)9CH=CH2 | CH3 | CH(CH3)2 | H | H | H | oil |
| CH(CH3)C6H5 | CH3 | CH(CH3)2 | H | H | H | oil |
| CH3 | —[CH(CH2)4—]— with CH3 | | H | H | H | 122–124 |
| CH2-C6H5 | —[CH(CH2)4—]— with CH3 | | H | H | H | 123–125 |

-continued

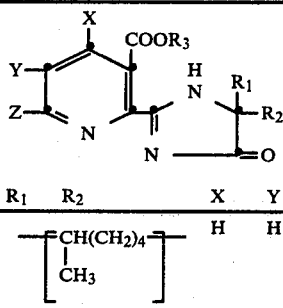

| R₃ | R₁ | R₂ | X | Y | Z | mp °C. |
|---|---|---|---|---|---|---|
| CH₂C≡CH | —[CH(CH₂)₄—CH₃]— | | H | H | H | 132–134.5 |
| CH₃ | CH₃ | CH(CH₃)₂ | H | H | Cl | 102.5–104.5 |
| CH₂COOCH₂CH₃ | CH₃ | CH(CH₃)₂ | H | H | H | 86–90 |
| CH₂COOH | CH₃ | CH(CH₃)₂ | H | H | H | 187–189 |
| CH₂COOCH₂C₆H₅ | CH₃ | CH(CH₃)₂ | H | H | H | 121.5–123 |
| CH₂COOH | CH₃ | CH(CH₃)₂ | H | H | H | 106–110 |
| CH₃ | CH₃ | CH(CH₃)₂ | H | H | H | 110–112 |
| CH₃ | CH₃ | CH(CH₃)₂ | H | H | H | 110.5–114  $[\alpha]_D = +27.41°$ |
| CH₂C₆H₅ | CH₃ | CH(CH₃)₂ | H | H | H | 102–105  $[\alpha]_D = +27.28°$ |
| CH₂C₆H₅ | CH₃ | CH(CH₃)₂ | H | H | H | 104–107  $[\alpha]_D = +13.08°$ |
| CH₃ | CH₃ | CH(CH₃)₂ | H | H | N(CH₃)₂ | 184.5–185.5  $[\alpha]_D = +12.76°$ |

EXAMPLE 8

Preparation of the Hydrochloride salt of methyl-2-(5-isopropyl-5-methyl-4-oxo-2-imidazolin-2-yl)-nicotinate To a stirred suspension of 3.0 g of the ester of Example 5 in 40 ml ether is added enough methylene chloride to obtain a solution. Dry hydrogen chloride is then passed into the solution for about 20 minutes. After 1 hour the mixture is filtered to remove the product which is washed with ether and dried to give 1.90 g of analytically pure hydrochloride salt and melting point equal to 195°–196° C.

EXAMPLE 9

Preparation of 2-(5-Isopropyl-5-methyl-4-oxo-2-imidazolin-2-yl)nicotinic acid

To 22.63 g ester of Example 5 in 100 ml water is added a solution containing 3.29 g sodium hydroxide in 25 ml water and the mixture heated under reflux with stirring for 1.5 hours. After standing at room temperature overnight, 6.8 ml concentrated hydrochloric acid is added causing a heavy precipitate to form. This is removed by filtration, washed with 20 ml water, followed by 30 ml ether and dried to give 19.27 g acid, mp 168°–170° C. This material is dissolved in 350 ml methylene chloride, filtered (to remove a small amount of the isomeric 2-acid) and concentrated to give 17.91 g of pure acid, mp 170°–172° C. The analytically pure sample is prepared by recrystallization of the material from acetone-hexane, mp 170°–172.5° C.

EXAMPLE 10

Preparation of 2-(5-Isopropyl-5-methyl-4-oxo-2-imidazolin-2-yl)nicotinic acid

To 1.0 g of the benzyl ester in 20 ml ethanol is added 50 mg 5% palladium on carbon catalyst and the mixture shaken in an atmosphere of hydrogen until one equivalent of hydrogen has been absorbed. The catalyst is removed by filtration, the solvent removed in vacuo and the residue crystallized from acetone-hexane to give the acid as described in Example 9.

The following acids are made by the above methods:

| R₁ | R₂ | mp °C. |
|---|---|---|
| CH₃ | C₂H₅ | 124–126° |
| —CH—(CH₂)₄— CH | | 180–183° |
| CH₃ | CH₃ | 204–205.5° |
| CH₃ | Δ | 198–200° |

EXAMPLE 11

Preparation of Calcium 2-(5-isopropyl-5-methyl-4-oxo-2-imidazolin-2-yl)nicotinate To 0.98 g of the acid of Example 9 partially dissolved in 10 ml water is added, with stirring 0.18 g calcium carbonate. After 10 minutes, the solution is filtered, the filtrate concentrated and the residue treated with ether to give a crystalline product which is dried at 40° C. and 25 mm pressure to give 0.88 g of the calcium salt mp 265° C.

The sodium, diisopropylammonium, and triethylammonium salts are prepared in a similar manner.

The following salts can be prepared by the above procedure using the appropriate acid and the oxide, carbonate, bicarbonate or hydroxide of the selected metal, alkali metal, alkaline earth metal, ammonia or aliphatic amine.

| Z+ | mp °C. |
|---|---|
| NH₃CH(CH₃)C₆H₅ | gum |
| NH₄ | sublines >168 |
| Ba/2 | >225 |
| Cu/2 | >225 |
| K | >225 |
| Li | >225 |
| Mg/2 | >225 |
| ⌬NH₂ (cyclohexyl) | — |
| C₆H₄-CH₂N(CH₃)₃ | oil |
| H₂N—(CH₂)₆NH₃ | oil |
| C₁₈H₃₅ | wax |
| n-C₁₂H₂₅NH₃ | 150–153 |
| (CH₃)₃CCH₂C(CH₃)₂NH₃ | — |
| (n-C₄H₉)₂NH₂ | — |
| HOCH₂CH₂NH₂CH₃ | — |
| ⌬NHCH₃ (pyrrolidine) | — |
| n-C₈H₁₇NH₃ | — |
| C₆H₄-CH₂NH₃ | — |
| C₆H₄-NH₂ | — |
| O⌬N—H₂ (morpholine) | — |
| C₆H₄-(CH₂)₄NH₃ | — |
| C₆H₄-(CH₂)₂NH₃ | — |
| (CH₃O)₂CHCH₂NH₃ | — |
| (C₂H₅OCH₂CH₂)NH₃ | — |
| CH₃O(CH₂)₃NH₃ | — |
| (HOCH₂CH₂)₂NH₂ | — |
| Fe/2 | >225 |
| Fe/3 | 155–158 |
| HOCH₂CH₂NH₃ | — |

-continued

| Z+ | mp °C. |
|---|---|
| ⌬NH₂ (piperidine) | — |
| (C₂H₅)₂NH₂ | — |
| (CH₃)₂CHNH₃ | — |
| CH₂=C(CH₃)CH₂NH₃ | — |
| (CH₃)₂CHCH₂NH₃ | — |
| CH₃OCH₂CH(CH₃)NH₃ | — |
| (CH₃)₃CNH₃ | — |

EXAMPLE 12

Preparation of Methyl 2-[(carbamoyl-1,2-dimethylpropyl)carbamoyl]nicotinate

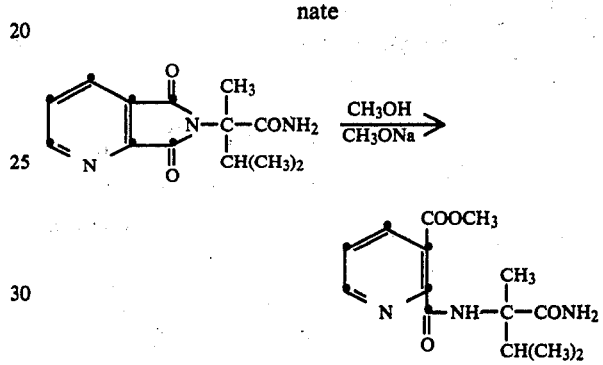

Sodium hydride (0.47 g of a 50% suspension in mineral oil) is reacted with 500 ml dry methanol under nitrogen. To this is added 51.4 g of the amide of Example 2 and the mixture stirred at room temperature overnight. The mixture is concentrated, the residue dissolved in methylene chloride and the solution washed first with 150 ml water followed by 150 ml brine. After drying (Na₂SO₄), the organic phase is concentrated and the residue crystallized from ether to give 47.85 g of product which is analytically pure mp 108°–145° C. with decomposition.

EXAMPLE 13

Preparation of Methyl 3-[1-carbamoyl-1,2-dimethylpropyl)carbamoyl]picolinate

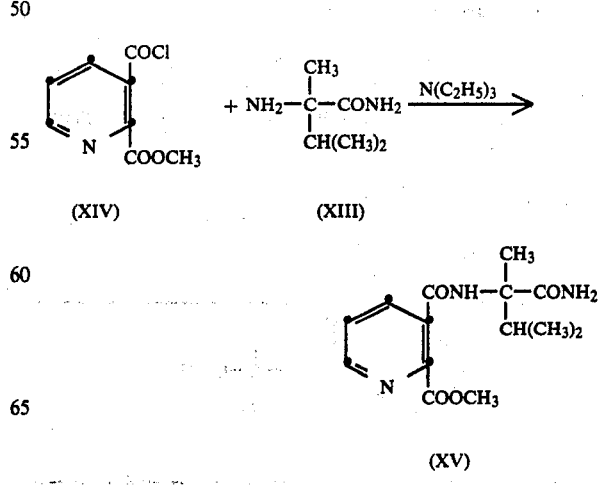

To a stirred mixture containing 25.5 g acid chloride [(Helv. Chem. Acta, 34, 488 (1951)] and 29.7 ml triethylamine in 200 ml methylene chloride is added, under nitrogen, dropwise a solution containing 13.93 g amino amide as disclosed in (U.S. Pat. No. 4,017,510) at such a rate that the temperature of the reaction mixture remains below 30° C. After 1 hour, the mixture is filtered, the solid washed with methylene chloride and dried to give 19.8 g product, mp 176°–177° C. (decomp). A sample recrystallized from nitromethane had mp 196°–196.5° C. (decomp) and analytically pure.

EXAMPLE 14

Preparation of 5,7-Dihydro-α-isopropyl-α-methyl-5,7-dioxo-6-H-pyrrolo[3,4-b]pyridine-6-acetic acid (-isomer)

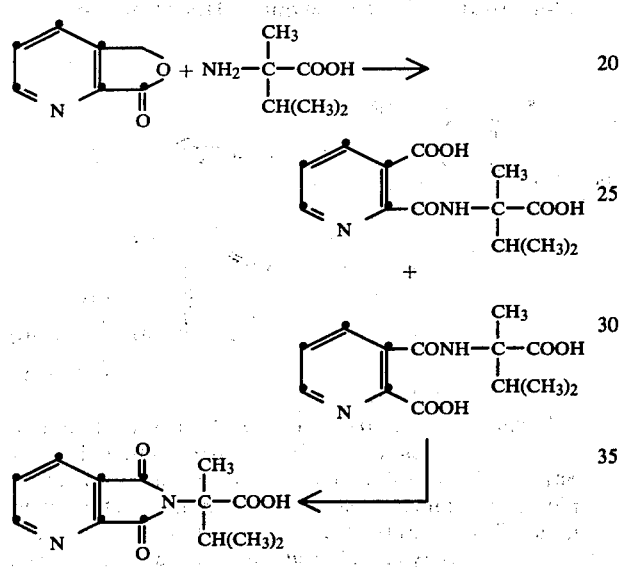

To a stirred suspension of 18.4 g of the anhydride in 760 ml of dry acetone is added, under nitrogen, 16.2 g of (+)-methylvaline. After stirring at room temperature for 48 hours, the mixture is filtered and the filtrate concentrated to give the crude intermediate. This material is dissolved in 500 ml acetic anhydride, a catalytic quantity of sodium acetate added and the mixture stirred at room temperature for 5 hours. After heating under reflux for 1.5 hours, the mixture is concentrated. The residue is dissolved in ethyl acetate and washed with water. The dried extract is concentrated to give a dark syrup. A sample is dissolved in ethyl acetate, treated with charcoal, filtered and concentrated. The residue is crystallized from methylene chloride to give the product, mp 122°–125° C. $[\alpha]_D^{25} = -7.73°$ C. (c=0.100, THF).

By essentially the same procedure and using the appropriate starting quinolinic anhydride and amino acid the following amides are prepared

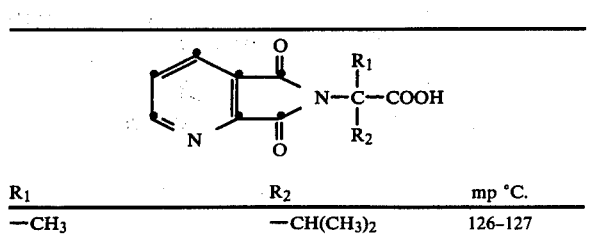

| R$_1$ | R$_2$ | mp °C. |
|---|---|---|
| —CH$_3$ | —CH(CH$_3$)$_2$ | 126–127 |

-continued

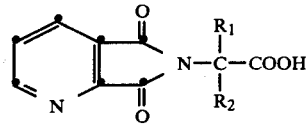

| R$_1$ | R$_2$ | mp °C. |
|---|---|---|
| CH$_3$ | CH$_2$CH(CH$_3$)$_2$ | $[\alpha]_D^{25} = +6.93$ (c = 0.100, THF) 174–176 |
| CH$_3$ | CH(CH$_3$)$_2$ | 196.5–198.5 |
| —CHCH$_2$CH$_2$CH$_2$CH$_2$— \| CH$_3$ | | 183–186 |

EXAMPLE 15

Preparation of 5,7-Dihydro-α-isopropyl-α-methyl-5,7-dioxo-6H-pyrrolo[3,4-b]pyridine-6-acetamide

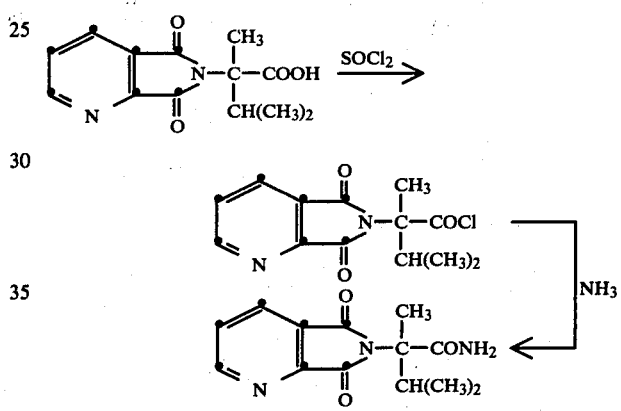

To a mixture containing 32 g of (−)-acid in 375 ml of toluene is added 2 ml of dimethylformamide followed by 13 ml of thionyl chloride. After heating at reflux for 1.25 hours, the mixture is concentrated in vacuo. The residue is dissolved in 350 ml of tetrahydrofuran, cooled to 0° C. and a slight excess of gaseous ammonia bubbled through the mixture. The solvent is removed in vacuo to leave a solid which is washed with water and air-dried. A portion of this solid is crystallized twice from ethyl acetate (with charcoal treatment) to give the desired product as a white crystalline solid, mp 188°–189° C. $[\alpha]_D^{25} = +3.59$ (c=0.0791, DMSO)

By essentially the same procedure and using the appropriate acid, the following amides are prepared.

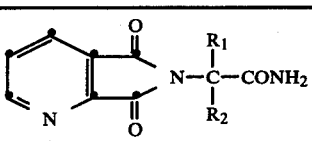

| R$_1$ | R$_2$ | mp °C. |
|---|---|---|
| CH$_3$ | CH(CH$_3$)$_2$ | 189.5–192 $[\alpha]_D^{25} = -3.02$ (c = 0.0744,DMSO) |
| CH$_3$ | CH$_2$CH(CH$_3$)$_2$ | 176–178 |

-continued

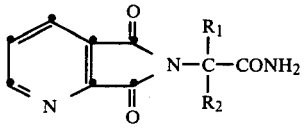

| R₁ | R₂ | mp °C. |
|---|---|---|
| —CHCH₂CH₂CH₂CH₂—<br>$\vert$<br>CH₃ | | 186–188 |

EXAMPLE 16

Preparation of 5-Butyl-N-(1-carbamoyl-1,2-dimethylpropyl)picolinamide

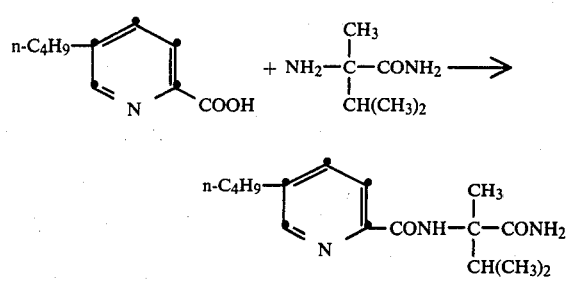

To a suspension of 20 g of acid in 200 ml of dry tetrahydrofuran is added with stirring 10.7 ml of ethyl chlorformate. The mixture is cooled to −10° C. and and 17.1 ml of triethylamine added dropwise so that the temperature does not exceed 0° C. After 10 minutes, a solution containing 14.3 g of the amino amide in 150 ml of dry tetrahydrofuran is added dropwise at 0° C. with stirring. The mixture is allowed to reach room temperature and after 2 hours, enough water added to dissolve the solid. The tetrahydrofuran is removed in vacuo. The aqueous residue is extracted with ethyl acetate, and after saturating with salt, extracted again. The organic phases are combined, washed with brine dried and concentrated. The residual oil crystallized. A portion was crystallized first from methylene chloride-hexane followed by ether-hexane to give analytically pure product mp 83°-86° C.

Using essentially the same procedures described above the following picolinic acids are prepared.

| X | Y | Z | mp °C. |
|---|---|---|---|
| H | CH₃ | H | 126–127.5° |
| H | H | CH₃ | |
| H | C₆H₅ | H | |
| H | NO₂ | H | |

EXAMPLE 17

Preparation of 2-(5-Butyl-2-pyridyl)-5-isopropyl-5-methyl-2-imidazolin-4-one

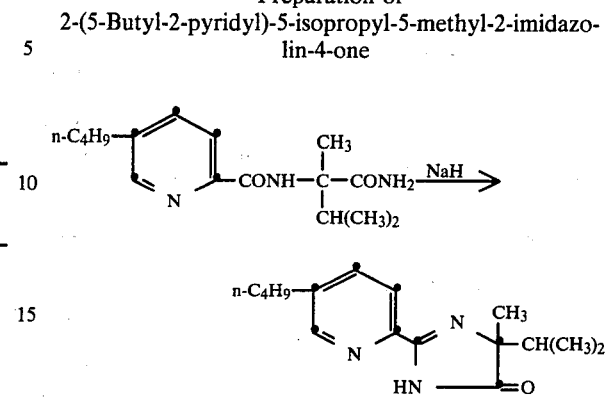

A stirred suspension of sodium hydride (2.4 g) in 250 ml of dry toluene is heated with stirring, under reflux under a Dean-Stark water Separator. To this mixture is added slowly 26.52 g of diamide. After the addition, heating is continued for 1.5 hours. After standing overnight, the reaction is quenched with water, the pH adjusted to 5 with hydrochloric acid and the phases separated. The aqueous phase is further extracted twice with ethyl acetate, the organic extracts combined, washed with brine, dried and concentrated.

The residue is recrystallized from hexane to give the pure product mp 60°-62° C.

Using essentially the same procedure, the following imidazolinones are prepared.

| X | Y | Z | mp °C. |
|---|---|---|---|
| H | C₆H₅ | H | |
| H | H | CH₃ | |
| H | CH₃ | H | |
| H | NO₂ | H | |

EXAMPLE 18

Preparation of 5-Butyl-2-(5-isopropyl-5-methyl-4-oxo-2-imidazolin-2-yl)nicotinic acid

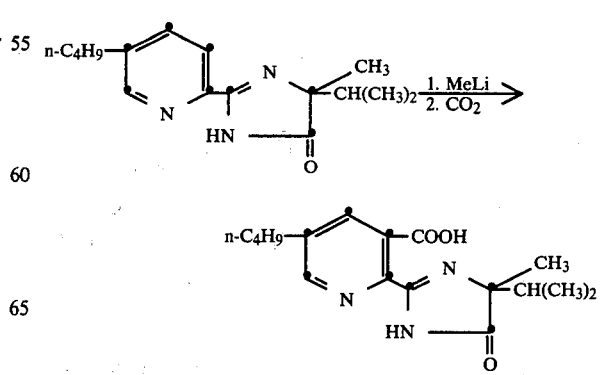

To a stirred solution containing 10.0 g imidazolinone in 100 ml dry tetrahydrofuran at −76° under nitrogen is added dropwise 47.3 ml of a 1.7 M solution of methyl lithium in ether. The mixture becomes very thick and 2 ml hexamethylphosphoramide and about 150 ml tetrahydrofuran is added. The mixture is allowed to warm to −10° C. and held at this temperature for 0.75 hour. The mixture is cooled to −70° and added to slurry of carbon dioxide in tetrahydrofuran. After stirring for 0.5 hour, water is added to the mixture, the pH adjusted to 2 with dilute sulfuric acid, and the product extracted into methylene chloride. The extract is washed with brine, dried and concentrated to give the product as a yellow solid. Recrystallization from methylene-chloride-hexane gave an analytically pure sample, mp 152°–154°.

Using essentially the same procedure as described above but substituting the appropriate imidazolinone for 2-(5-butyl-2-pyridyl)-5-isopropyl-5-methyl-2-imidazolinone, and using dimethylformamide and methyl iodide as well as carbon dioxide as electrophiles, the following imidazolinones are prepared:

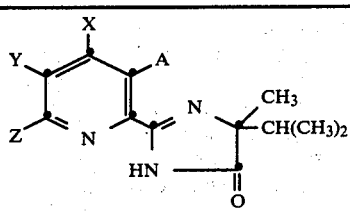

| A | X | Y | Z | mp °C. |
|---|---|---|---|---|
| COOH | Cl | H | H | 184–186 |
| COOH | H | CH$_3$ | H | 203.5–204.5 |
| COOH | H | C$_6$H$_5$ | H | 150–151.5 |
| CH$_3$ | H | H | H | 93–96 |
| CHO | H | H | H | 223–225 |
| COOH | H | H | C$_6$H$_5$ | 252–254 |
| COOH | H | CH$_2$O—Si(CH$_3$)$_2$—C(CH$_3$)$_3$ | H | 82–85 |
| COOH | H | C$_2$H$_5$ | H | |

EXAMPLE 19

Preparation of 2-(5-Isopropyl-5-methyl-4-oxo-2-imidazolin-2-yl)-3-pyridineacetic acid

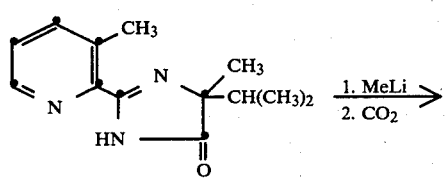

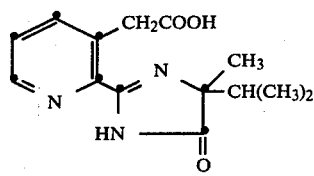

Using essentially the same procedure as described in Example 18 but substituting 5-isopropyl-5-methyl-2-(3-methyl-2-pyridyl)-2-imidazolin-4-one for 5-isopropyl-5-methyl-2-(5-n-butyl-2-pyridyl)-2-imidazolin-4-one, there is obtained the desired pyridine-acetic acid, mp 173 (dec.).

EXAMPLE 20

Preparation of Methyl 2-(5-isopropyl-5-methyl-4-oxo-2-imidazolin-2-yl)-6-phenoxynicotinate

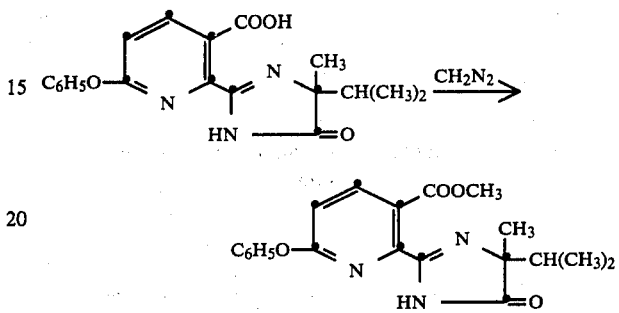

A solution of the acid in ether is treated with excess diazomethane. After a few minutes excess diazomethane is removed by warming. The solvent is removed and the residue crystallized from ether hexane to give the desired methyl ester mp 128°–131° C.

Using essentially the same conditions as those described above, the following methyl esters are prepared starting with the appropriate acid.

| X | Y | Z | mp °C. |
|---|---|---|---|
| H | H | —OC$_6$H$_5$ | 128–131 |
| H | —C$_4$H$_9$—n | H | 69–71.5 |
| Cl | H | H | 110–113 |
| H | H | OCH$_2$C$_6$H$_5$ | 187–188 |
| H | H | OC$_2$H$_5$ | 126–129 |
| OC$_6$H$_5$ | H | H | 175–177 |
| H | CH$_3$ | H | 129–130.5 |
| H | C$_6$H$_5$ | H | |
| H | H | C$_6$H$_5$ | |
| OCH$_2$C$_6$H$_5$ | H | H | 164–171 |
| H | C$_2$H$_5$ | H | |
| H | CH$_2$OH | H | 146–147 |

EXAMPLE 21

Preparation of 4 [2-(5-Isopropyl-5-methyl-4-oxo-2-imidazolin-2-yl)nicotinoyl]morpholine

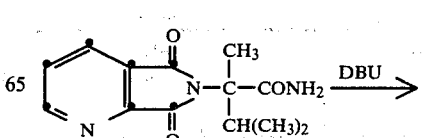

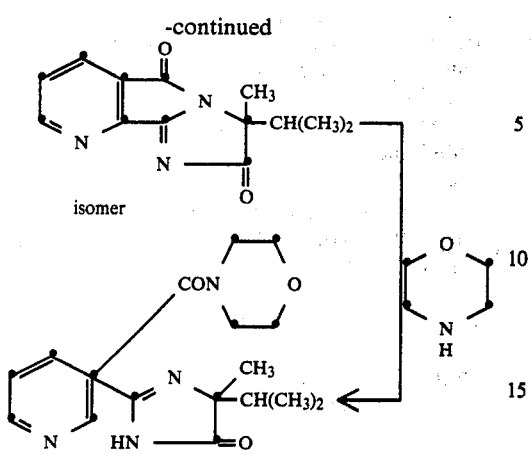
isomer

The cyclization of the amide is accomplished by heating 7.83 g of amide in 150 ml of toluene and 0.45 ml of 1,8-diazabicyclo[5,4,0]undec-7-ene under a Dean-Stark water Separator for 2 hours as described in Example 4. The separator is removed, 4 ml of morpholine is added and heating continued for 3 hours. The mixture is concentrated and the residue chromatographed on silica gel in ethyl acetate. The product is eluted first and this material is recrystallized from ether-hexane to give pure amide mp 143°–145.5° C.

By substituting the appropriate amine for morpholine, the following amides are prepared.

| $R_6$ | mp °C. |
|---|---|
| —CH₂C≡CH | 171–173.5 |
| ![4-chlorophenyl] | 227.5–228.5 |
| —CH₂CH₂OH | 174.5–175.5 |

EXAMPLE 22

Preparation of N-(2-chloroethyl)-2-(5-isopropyl-5-methyl-4-oxo-2-imidazolin-2-yl)nicotinamide

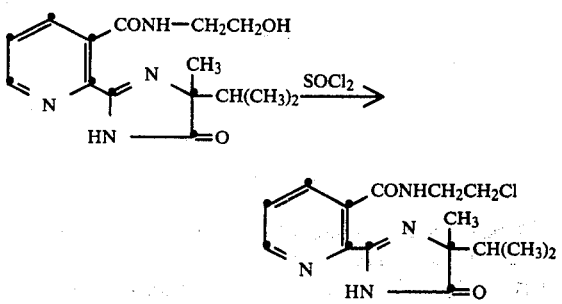

A mixture containing 4.04 g of hydroxyethylamide and 8.2 ml of thionyl chloride in 250 ml of methylene chloride is heated at reflux for 3.5 hours. The mixture is cooled, poured into water and the aqueous phase made basic with sodium carbonate. The mixture is shaken, the organic phase separated, washed with water, dried and concentrated to leave a white solid which is recrystallized from toluene to give the desired chloroethylamide as a white crystalline solid, melting partially at 128.5° C. with complete melting at 157° C.

EXAMPLE 23

Preparation of 2-(5-Isopropyl-5-methyl-4-oxo-2 imidazolin-2-yl)nicotinamide

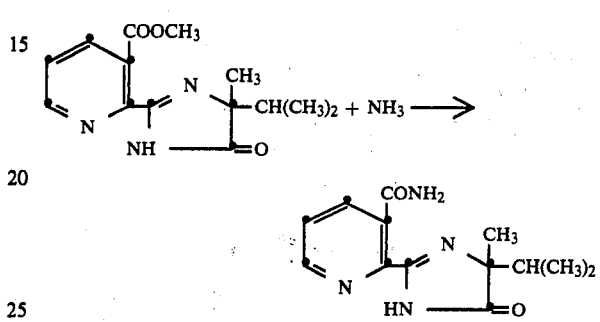

A solution containing 10.0 g of ester in 50 ml of tetrahydrofuran is added to 100 ml of liquid ammonia in a glass bomb. The bomb is sealed and the contents heated at 100° C. for 16 hours. After cooling, the ammonia is evaporated and the residue concentrated. This residue is combined with material from similar reactions using 5 g and 7 g of the ester. These are crystallized from ethyl acetate to give 5 g of product. The filtrate is concentrated after treatment with charcoal to give a further 15.7 g of product.

Two recrystallizations of a sample from ethyl acetate gives the pure nicotinamide as a white crystalline solid mp 178°–182° C.

EXAMPLE 24

Preparation of 2-(5-Isopropyl-5-methyl-4-oxo-2-imidazolin-2-yl)nicotinonitrile

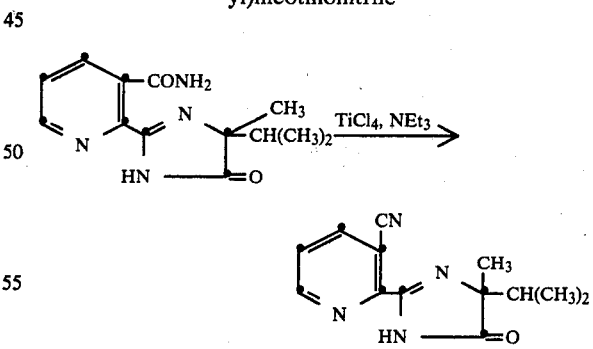

To 75 ml of ice-cold tetrahydrofuran under nitrogen is added with stirring 12 ml of titanium tetrachloride in 20 ml of carbon tetrachloride at such a rate that the temperature does not exceed 5° C. This is followed by the addition of 5.2 g of the amide in 75 ml of tetrahydrofuran again maintaining a temperature of <5° C. Finally, 17 ml of triethylamine in 5 ml of tetrahydrofuran is added to the mixture under the same conditions. After 1.5 hours at 5° C., the mixture is stirred overnight at room temperature. Water (100 ml) is cautiously added at 0° C., the upper organic phase is separated and the aqueous phase extracted with methylene chloride (4×100 ml). The combined extracts are washed with brine, dried and concentrated. The solid residue is recrystallized from hexane-methylene-chloride to give the nicotinonitrile as a tan solid, mp 144°–148° C. The analytically pure compound has mp 148°–150° C.

EXAMPLE 25

Preparation of 2-[5-(hydroxymethyl)-2-pyridyl]-5-isopropyl-5-methyl-2-imidazolin-4-one

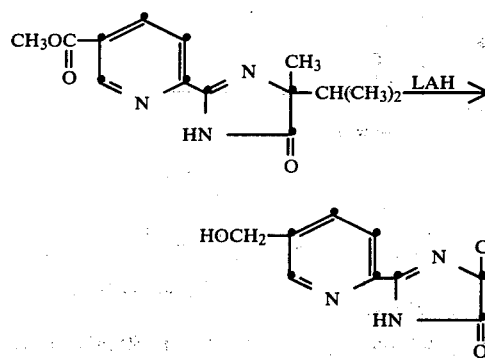

To a stirred slurry of 23 g lithium aluminum hydride in 250 ml tetrahydrofuran under nitrogen at −70° C. is added dropwise 46.8 g of the ester in 350 ml tetrahydrofuran. The mixture is warmed to room temperature, 73 ml of a saturated ammonium chloride solution added cautiously with vigorous stirring, the mixture filtered and the solid washed with tetrahydrofuran. The filtrate is concentrated to leave a gum. This is chromatographed on silica gel and the product eluted by ethyl acetate, mp 101°–104° C.

EXAMPLE 26

Preparation of 2-[5(tert-butyldimethylsiloxy)methyl-2-pyridyl]-5-isopropyl-5-methyl-2-imidazolin-4-one

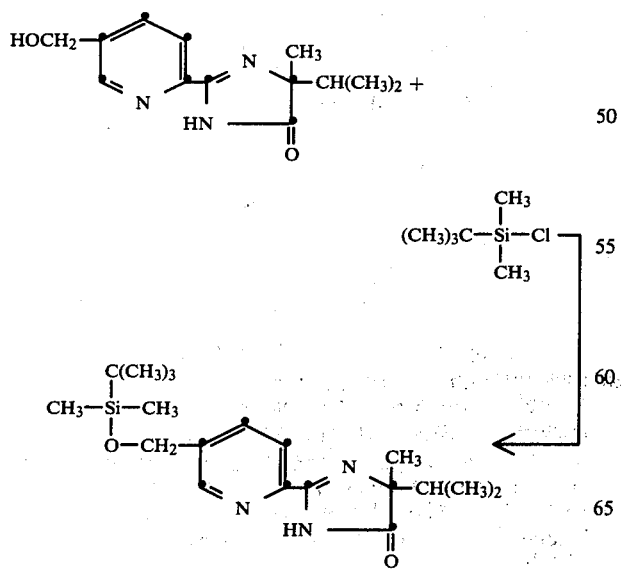

To a stirred solution containing 2.03 g alcohol in 3.5 ml dimethylformamide under nitrogen is added 0.68 g imidazole followed by 3.1 g t-butyldimethylsilyl chloride. The mixture is kept at 35° C. for 10 hours and room temperature for 10 hours. Saturated sodium sulfate is added and the aqueous mixture extracted with ether. The extract is washed with brine, dried and evaporated. The pure product is isolated as a gum by chromatography of the crude product on silica gel and elution with methylene chloride followed by ether.

EXAMPLE 27

Preparation of 5-(Hydroxymethyl)-2-(5-isopropyl-5-methyl-4-oxo-2-imidazolin-2-yl)nicotinic acid

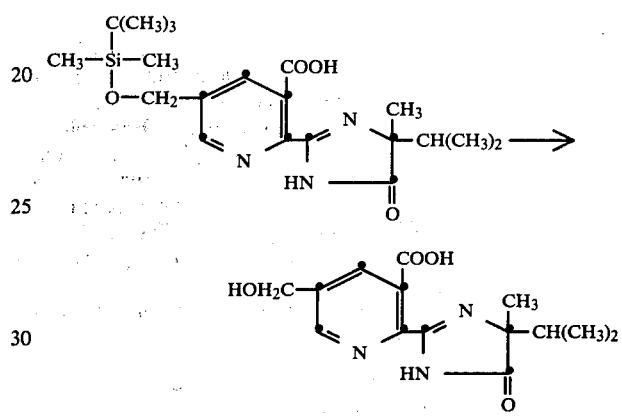

A solution containing 0.29 g silyl ether in 10 ml 80% aqueous acetic acid is heated on the steam bath for 0.5 hours. The mixture is concentrated and the residue dried azeotropically with toluene. The residue, a gum, is crystallized from methylene chloride-hexane. The pure product has mp 170°–171.5° C.

EXAMPLE 28

Preparation of Methyl 2-(1-acetyl-4-isopropyl-4-methyl-5-oxo-2-imidazolin-2-yl)nicotinate

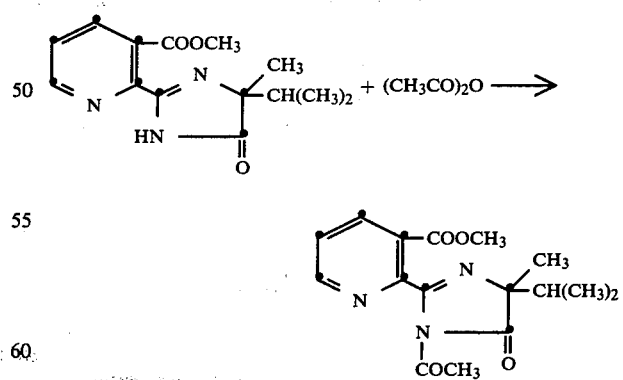

A solution containing 10 g methyl 2-(5-isopropyl-5-methyl-4-oxo-2-imidazolin-2-yl)nicotinate in 100 ml acetic anhydride is heated under reflux for 16 hours. The mixture is concentrated and the residue crystallized from ether-hexane to give the N-acetyl derivative, mp 88°–90° C. This is the mp of analytically pure material.

Using essentially the same conditions as those described above, the following N-substituted imidazolinones are prepared by reacting the appropriate imidazolinyl nicotinate with the appropriate acyl anhydride, acyl halide, sulfonyl halide, alkyl halide or sulfate either alone or in a solvent such as pyridine or toluene.

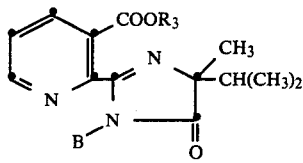

| $R_3$ | B | mp °C. |
|---|---|---|
| $CH_3$ | $CH_3$ | oil |
| $CH_3$ | $COC(CH_3)_3$ | 85–87 |
| $CH_3$ | $COC_{11}H_{23}$—n | oil |
| $CH_3$ | $COC_6H_5$ | 104–107 |
| $CH_3$ | $COC_2H_5$ | 90–92.5 |
| $CH_3$ | $COCH_2Cl$ | 98–100 |
| $CH_2C_6H_5$ | $COC_2H_5$ | oil |
| $CH_2C_6H_5$ | $COC(CH_3)_3$ | oil |
| $CH_2C_6H_5$ | $COCH_2Cl$ | oil |
| $CH_3$ | $SO_2CH_3$ | 115–118 |
| $CH_2$≡CH | $COCH_3$ | 125–127 |
| $CH_2C$≡CH | $COCH_2Cl$ | 118–122 |
| $CH_2C$≡CH | $COC_6H_5$ | 118–120 |
| $CH_2C$≡CH | $COC(CH_3)_3$ | 101–104 |
| $CH_3$ | $COOC_2H_5$ | oil |
| $CH_3$ | $SO_2$—⌬—$CH_3$ | 114–118 |
| $CH_2C_6H_5$ | $COC_6H_5$ | 117–125 |
| $CH_2C$≡CH | $COC_2H_5$ | 85–88 |
| $CH_3$ | $CO$—⌬—$Cl$ | 122–125 |
| $CH_3$ | $CO$—⌬—$OCH_3$ | 119.5–121.5 |
| $CH_3$ | $CO$—⌬—$NO_2$ | 148–151 |

EXAMPLE 29

Preparation of Methyl 2-(1-acetyl-4-isopropyl-4-methyl-5-oxo-2-imidazolin-2-yl)nicotinate-1-oxide

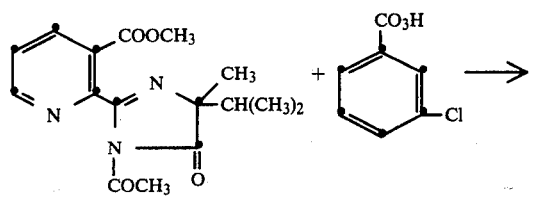

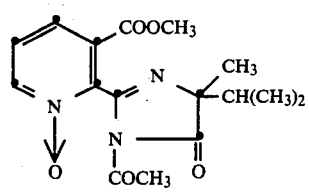

To a solution containing 40 g (126 mmoles) of the nicotinate in 500 ml methylene chloride is added 30 g of 80–90% pure (139 mmoles based on 80% purity) m-chloroperbenzoic acid. After heating at reflux overnight, excess peracid is destroyed by the addition of excess 1-hexene. The solution is washed with saturated sodium bicarbonate solution, dried and concentrated. The residue is crystallized from methylene chloride-hexane-ether to give 18.3 g of the desired N-oxide, mp 92°–100° C. The analytically pure N-oxide has mp 95°–99° C.

EXAMPLE 30

Preparation of Methyl 2-(5-isopropyl-5-methyl-4-oxo-2-imidazolin-2-yl)nicotinate-1-oxide

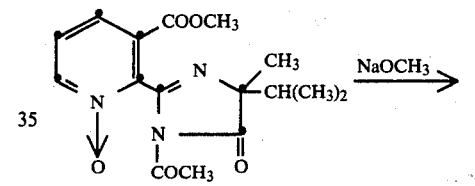

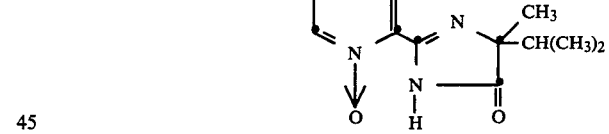

To a solution of 30 g of the N-acetyl compound in 200 ml methanol is added approximately 0.5 g sodium methoxide. After stirring for two hours, the product is removed by filtration and air dried, mp 197°–201° C. The analytically pure sample which had been recrystallized from acetone-hexane has mp 200°–201° C.

EXAMPLE 31

Preparation of Methyl 6-chloro-2-(5-isopropyl-5-methyl-4-oxo-2-imidazolin-2-yl)nicotinate

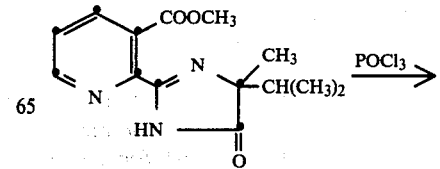

-continued

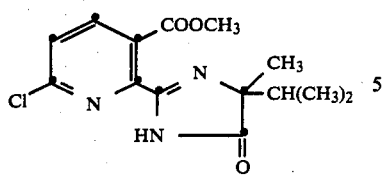

A solution containing 22.0 g N-oxide in 135 ml phosphorus oxychloride is heated under reflux for four hours. After standing at room temperature overnight, excess phosphorus oxychloride is removed in vacuo and the residue treated with xylene and again concentrated. The residue is dissolved in methylene chloride and treated with water, the pH adjusted to 5 with sodium carbonate and ether added to make the organic layer the upper layer. The layers are separated and the aqueous phase reextracted twice with ether. The combined organic extracts are washed with brine, dried and concentrated. The residue is chromatographed on 250 g of silica gel in a mixture of ether and hexane to give 10.6 g of the desired product. This is recrystallized from ether-hexane to give 8.95 g of the 6-chloro derivative, mp 104°–106° C. The analytically pure sample melted at 102.5°–104.5° C.

EXAMPLE 32

Preparation of 6-Chloro-2-(5-isopropyl-5-methyl-4-oxo-2-imidazolin-2-yl)nicotinic acid

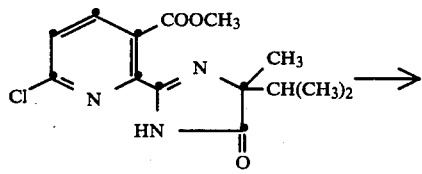

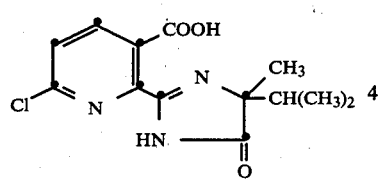

A suspension of 3.0 g of the ester in 5.8 ml of 2 N sodium hydroxide, 5 ml water and 3 ml methanol is warmed to 35° C. to obtain a clear solution. After stirring the solution for three hours, it is cooled, extracted with ether and the organic phase discarded. The pH of the aqueous phase is adjusted to 2 with 6 N hydrochloric acid and then sodium bicarbonate solution added to bring the pH to 4. The aqueous phase is extracted twice with methylene chloride, the pH of the aqueous phase adjusted to 2 and again extracted twice with methylene chloride. The organic phases are combined, dried and concentrated and the residue crystallized from methylene chloride-hexane to give the analytically pure acid, mp 154°–157° C.

Following the above procedure but substituting the 5-bromo ester for the 6-chloro ester yields 5-bromo-2-(5-isopropyl-5-methyl-4-oxo-2-imidazolin-2-yl)nicotinic acid, mp 211°–213° C.

EXAMPLE 33

Preparation of 6-(Benzyloxy)-2-(5-isopropyl-5-methyl-4-oxo-2-imidazolin-2-yl)nicotinic acid

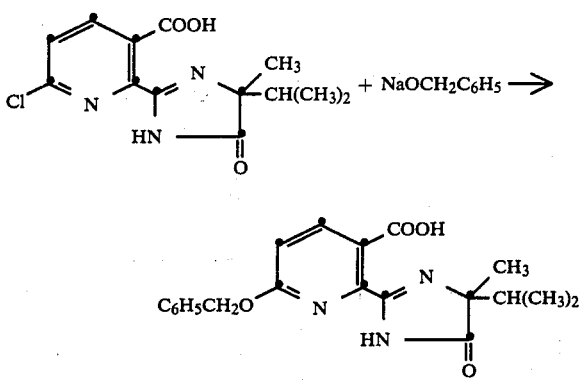

To sodium hydride (from 0.34 g 50% sodium hydride in oil) in 2 ml of N-methyl pyrolidone is added with stirring and under nitrogen 2 ml benzyl alcohol. After the formation of the alkoxide is complete, 0.6 g of the chloro acid is added and the mixture heated at 165°–175° for five hours.

After cooling, the mixture is diluted with water, the pH thereof adjusted to 1 with 1 N hydrochloric acid and then back to pH 8 with saturated sodium bicarbonate. The mixture is extracted twice with ether and the ether discarded. The pH of the aqueous phase is adjusted to 5 and extracted several times with methylene chloride. The extracts are combined, dried and concentrated. Crystallization from ether-hexane gives the 6-benzyloxy derivative mp 205°–207° C.

Using essentially the same conditions as described above, and using the appropriate 4- or 6-chloro-2-(5-isopropyl-5-methyl-4-oxo-2-imidazolin-2-yl)nicotinic acid and appropriate sodium alkoxide, phenoxide or thioalkoxide, the following imidazolinyl nicotinic acids are prepared.

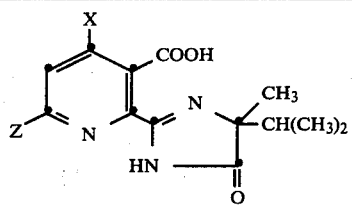

| X | Z | Mp °C. |
|---|---|---|
| H | OCH3 | 190–191.5 |
| OC6H5 | H | 196–198 |
| H | OC6H5 | 182.5–185.5 |
| H | OC2H5 | 190–191.5 |
| H | SCH3 | 188.5–190 |
| OCH2C6H5 | H | 172–174 |
| H | OCH2C6H5 | 205–207 |

EXAMPLE 34

Preparation of
4-Hydroxy-2(5-isopropyl-5-methyl-4-oxo-2-imidazolin-2-yl)nicotinic acid

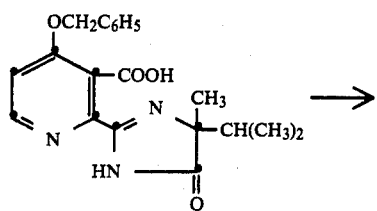

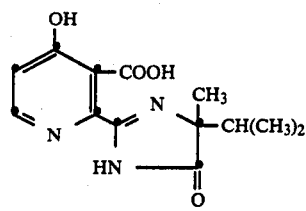

To 15 ml concentrated sulfuric acid is added slowly, with stirring 1.55 g of the benzyloxy derivative. To this mixture is added 7 ml ethylenedichloride. After 16 hours at room temperature, the mixture is poured over ice, the pH adjusted to 4 with dilute sodium hydroxide and extracted with ethyl acetate. The extract was dried and concentrated to leave a tan solid which is recrystallized from methylene chloride-ether, mp 210°–211° C.

EXAMPLE 35

Preparation of
2-Isopropyl-2-methyl-5H-imidazo[1',2':1,2]pyrrolo[3,4-b]pyridine-3(2H),5-dione

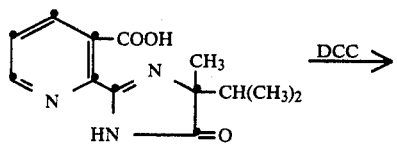

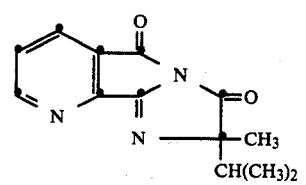

To a solution containing 50.9 g of dicyclohexylcarbodiimide in 600 ml of dry methylene chloride is added, while stirring, 60 g of the acid at such a rate that the temperature does not exceed 32° C. After stirring at room temperature for 2.5 hours, the mixture is filtered and the filtrate concentrated to give a white solid. This solid is recrystallized from methylene chloride to give 57.4 g of the dione, mp 125°–128.5° C. The analytically pure dione melts at 132°–134° C.

EXAMPLE 36

Preparation of the Acetone oxime ester of
2-(5-isopropyl-5-methyl-4-oxo-2-imidazolin-2-yl)nicotinic acid

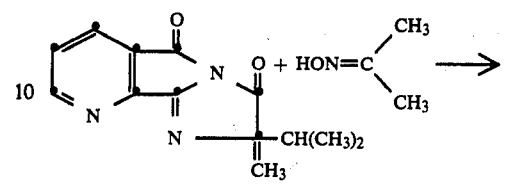

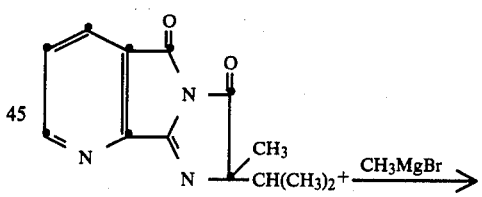

To a solution containing 2.0 g of the 3,5-dione in 15 ml of toluene is added 0.6 g of acetone oxime. The mixture is heated and stirred at 50°–60° C. for 2.75 hours. After stirring overnight at room temperature, the solvent is removed and the residue chromatographed on silica gel using 10% acetonitrile in methylene chloride followed by 30% acetonitrile in methylene chloride as the eluent. Toluene is removed from the fractions containing the product and the product collected. This is recrystallized from methylene chloride-hexane to give analytically pure oxime ester mp 117°–119.5° C. The ester from 2,2,2-trichloroethanol mp 114°–116° C. is prepared in essentially the same manner.

EXAMPLE 37

Preparation of
2-(3-Acetyl-2-pyridyl)-5-isopropyl-5-methyl-2-imidazolin-4-one

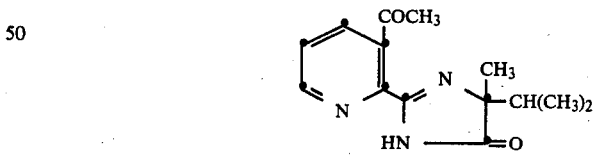

To a stirred solution containing 10.0 g of the dione in 100 ml of dry tetrahydrofuran under nitrogen and −78° C. is added dropwise 15.1 ml of a 3 M solution of methyl magnesium bromide in ether. A temperature of < −60° C. is maintained during the addition. After the addition, stirring is continued at −78° C. and then the mixture warmed slowly to room temperature. The mixture is diluted with an equal volume of water, the pH adjusted to 4 with glacial acetic acid and extracted three times with methylene chloride. The combined extracts are dried and concentrated. The residue is chromatographed on silica gel with ether. Concentration of the appropriate fractions give 6.1 g of product as a crystalline solid mp 104°–108° C. An analytically pure sample has mp 103°–105° C.

Using essentially the same procedure as described above but substituting phenyl lithium or sodium trimethyl phosphonoacetate for methyl magnesium bromide, the following imidazolinones are prepared.

| A | mp °C. |
|---|---|
| COC₆H₅ | 138–140.5 |
| COCH(COOCH₃)(P(OCH₃)₂=O) | 131.5–134 |

EXAMPLE 38

Preparation of 2-[3-(Hydroxymethyl)-2-pyridyl]-5-isopropyl-5-methyl-2-imidazolin-4-one

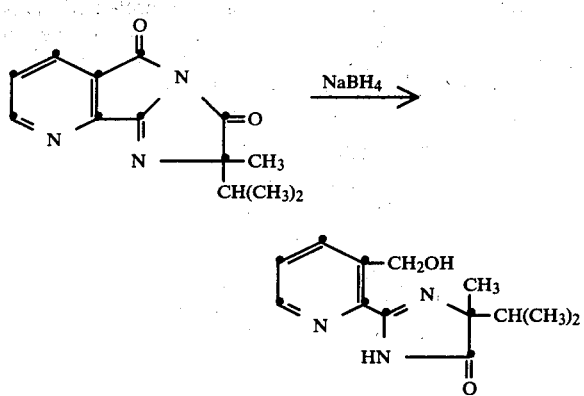

To a stirred solution of 0.32 g sodium borohydride in 25 ml absolute ethanol at 0° C. is added during 10 minutes with stirring a solution containing 2.0 g dione in 25 ml dry tetrahydrofuran. The mixture is then stirred a further three hours at room temperature. The mixture is poured into 200 ml ice water, extracted with methylene chloride, the extract dried and concentrated. The residue is crystallized from methylene-chloride-hexane to give the desired product. The analytically pure sample has mp 145°–149° C.

EXAMPLE 39

Evaluation Of Test Compounds As Sugar Yield Enhancing Agents For Plants

In the following tests 2-(5-isopropyl-5-methyl-4-oxo-2-imidazolin-2-yl)nicotinic acid is evaluated and compared with the isopropylamine salt of N-(phosphonomethyl)glycine (i.e. the isopropylamine salt of glyphosate) for control of rhizomatous johnsongrass. Glyphosate is a commercially available ripening agent for sugarcane and known as a sugar yield enhancing agent therefore. In these tests the compounds being evaluated are formulated as 2% aqueous solutions and applied to the foliage of johnsongrass using wick applicators purchased from a commercial vendor. The johnsongrass plants used in these evaluations are grown in separate pots in the greenhouse. Plants selected for test purposes are 24 inches and 32 inches in height. The wick applicators are made from 2 inch I.D. polyvinylchloride pipe 20 inches in length and provide an effective wick length of 18 inches. The applicators are arranged above a continuous belt upon which the potted plants are placed for application of the test solutions. The wicks are set 18 inches above the belt for application of test solutions to 24 inch johnsongrass plants and 24 inches above the belt for application to 32 inch plants.

The glyphosate formulation is a commercial composition containing 41% by weight of the isopropylamine salt of N-(phosphonomethyl)glycine and 59% by weight inert ingredients. The compounds are described in U.S. Pat. No. 3,799,758. The 2% by weight solution of this compound is prepared by admixing 48.8 ml of the glyphosate formulation with 951.2 ml of water.

The compound of the invention is prepared by dispersing 23.45 parts by weight of 2-(5-isopropyl-5-methyl-4-oxo-2-imidazolin-2-yl)nicotinic acid in 69.05 parts by weight of N-methylpyrrolidone and 7.5 parts by weight of nonylphenoxy polyethoxy ethanol. To prepare a 2% aqueous solution of this compound 89.7 ml of the above-formulation is admixed with 910.3 ml of water.

Three untreated johnsongrass plants from each group, i.e. 24 inch and 32 inch plants, are used as checks. Six plants per treatment are used for the evaluations which involves placing the potted plants on the moving continuous belt. The plants are carried by the belt toward the wick applicator where approximately one half, i.e. the upper portion, of the plant is brushed against the wick of the applicator which is used for dispensing the test solution. The treated plants were then turned 180° and placed on the continuous belt and again passed under the applicator thereby applying the test solution to the opposite side of the plants foliage. After treatment, the plants are placed in the greenhouse where they are cared for in accordance with conventional greenhouse practices.

Eight days after treatment the plants are examined and it is noted that all plants, both 24 inch and 32 inch, treated with the 2% solutions of either the isopropylamine salt of glyphosate or the 2-(5-isopropyl-5-methyl-4-oxo-2-imidazolin-2-yl)nicotinic acid are exuding a sugar solution in discrete droplets along the plant stems. This exudation has been previously observed on glyphosate treated johnsongrass and has correlated positively with an increase in sugar content from sugarcane when glyphosate is applied to sugarcane at rate of from 0.25 to 2.0 kg/ha. Thus, the compounds of the invention in the present application, as represented by 2-(5-isopropyl-5-methyl-4-oxo-2-imidazolin-2-yl)nicotinic acid, are effective for increasing sugar yields in plants such as sugarcane.

Similar results are obtained with the sodium, potassium and diisopropylamine salts of 2-(5-isopropyl-5-methyl-4-oxo-2-imidazolin-2-yl)nicotinic acid, also with methyl-2-(5-isopropyl-5-methyl-4-oxo-2-imidazolin-2-yl)nicotinate; 2-(5-ethyl-5-methyl-4-oxo-2-imidazolin-2-yl)nicotinic acid; calcium 2-(5-isopropyl-5-methyl-4-oxo-2-imidazolin-2-yl)nicotinate; 2-Propynyl 2-(5-isopropyl-5-methyl-4-oxo-2-imidazolin-2-yl)nicotinate; furfuryl 2-(5-isopropyl-5-methyl-4-oxo-2-imidazolin-2-yl)nicotinate; sodium 2-(5-isopropyl-5-methyl-4-oxo-2-imidazolin-2-yl)nicotinate; isopropylammonium 2-(5-isopropyl-5-methyl-4-oxo-2-imidazolin-2-yl)nicotinate; 6-chloro-2-(5-isopropyl-5-methyl-4-oxo-2-imidazolin-2-yl)nicotinic acid; 6-methyl-2-(5-isopropyl-5-methyl-4-oxo-2-imidazolin-2-yl)nicotinic acid.

We claim:
1. A method for increasing sucrose yields from sugarcane comprising applying to the foliage of said sugarcane about 2 weeks to 4 weeks prior to first harvest an effective amount of a compound having the formula:

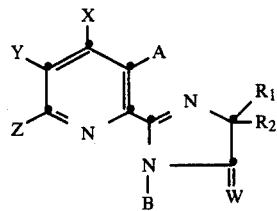

(I)

wherein
$R_1$ is $C_1$–$C_3$ alkyl;
$R_2$ is $C_1$–$C_2$ alkyl;
A is $COOR_3$;
$R_3$ is hydrogen, methyl or furfuryl; $C_3$alkynyl; or,
A cation of alkali metals, alkaline earth metals, ammonium or organic ammonium;
B is H;
W is O;
X and Y are hydrogen;
Z is hydrogen chlorine or methyl; the optical isomers thereof, or except when $R_3$ is a salt-forming cation, the acid addition salts thereof.

2. A method according to claim 1 wherein said compound is applied to the foliage of sugarcane as a liquid spray in sufficient amount to provide from 0.016 kg/ha to 4.0 kg/ha of said compound.

3. A method according to claim 1 wherein said compound is applied in the form of an aqueous spray and in sufficient amount to provide from 0.05 kg/ha to 2.0 kg/ha of said compound.

4. A method according to claim 1 wherein said compound is 2-(5-isopropyl-5-methyl-4-oxo-2-imidazolin-2-yl)nicotinic acid.

5. A method according to claim 1 wherein said compound is 2-(5-ethyl-5-methyl-4-oxo-2-imidazolin-2-yl)-nicotinic acid.

6. A method according to claim 1 wherein said compound is the diisopropylamine salt of 2-(5-isopropyl-5-methyl-4-oxo-2-imidazolin-2-yl)nicotinic acid.

7. A method according to claim 1, calcium 2-(5-isopropyl-5-methyl-4-oxo-2-imidazolin-2-yl)-nicotinate.

* * * * *